United States Patent
Lang et al.

Patent Number: 5,471,880
Date of Patent: Dec. 5, 1995

[54] METHOD AND APPARATUS FOR ISOLATING AND IDENTIFYING PERIODIC DOPPLER SIGNALS IN A TURBINE

[75] Inventors: George F. Lang, Lansdale; Robert L. Leon, Maple Glen, both of Pa.

[73] Assignee: Electric Power Research Institute, Palo Alto, Calif.

[21] Appl. No.: 234,192

[22] Filed: Apr. 28, 1994

[51] Int. Cl.⁶ .................................................. G01N 29/12
[52] U.S. Cl. ............................................. 73/660; 364/508
[58] Field of Search .................. 73/579, 593, 660, 73/658, 659; 364/508

[56] References Cited

U.S. PATENT DOCUMENTS

| | | | |
|---|---|---|---|
| 4,389,891 | 6/1983 | Fournier | 43/579 |
| 4,413,519 | 11/1983 | Bannister et al. | 73/660 |
| 4,422,333 | 12/1983 | Leon | 73/660 |
| 4,559,828 | 12/1985 | Liszka | 73/658 |
| 4,573,358 | 3/1986 | Luongo | 73/660 |
| 4,593,566 | 6/1986 | Ellis | 73/660 |
| 4,722,226 | 2/1988 | Edmond | 73/660 |
| 4,887,468 | 12/1989 | McKendree et al. | 73/660 |
| 4,896,537 | 1/1990 | Osborne | 73/660 |
| 4,934,192 | 6/1990 | Jenkins | 73/660 |
| 4,955,269 | 9/1990 | Kendig et al. | 73/577 |
| 4,996,880 | 3/1991 | Leon et al. | 73/660 |
| 5,141,391 | 8/1992 | Acton et al. | 415/119 |
| 5,148,711 | 9/1992 | Twerdochlib et al. | 73/660 |
| 5,152,172 | 10/1992 | Leon et al. | 73/579 |
| 5,206,816 | 4/1993 | Hill et al. | 364/508 |

*Primary Examiner*—Robert Raevis
*Assistant Examiner*—Rose M. Finley
*Attorney, Agent, or Firm*—Panitch Schwarze Jacobs & Nadel

[57] ABSTRACT

An improved method and apparatus for detecting and identifying one or more resonantly vibrating blades of a turbine through the use of acoustic sensors imbedded in the stationary casing of the turbine is disclosed. The acoustic sensor signals are processed to separate the characteristic Doppler waveform from the accompanying random noise and periodic noise. Improved signal processing techniques which involve the evaluation of both an information-bearing resonant signal and its Hilbert transform via direct synthesis are disclosed.

38 Claims, 14 Drawing Sheets

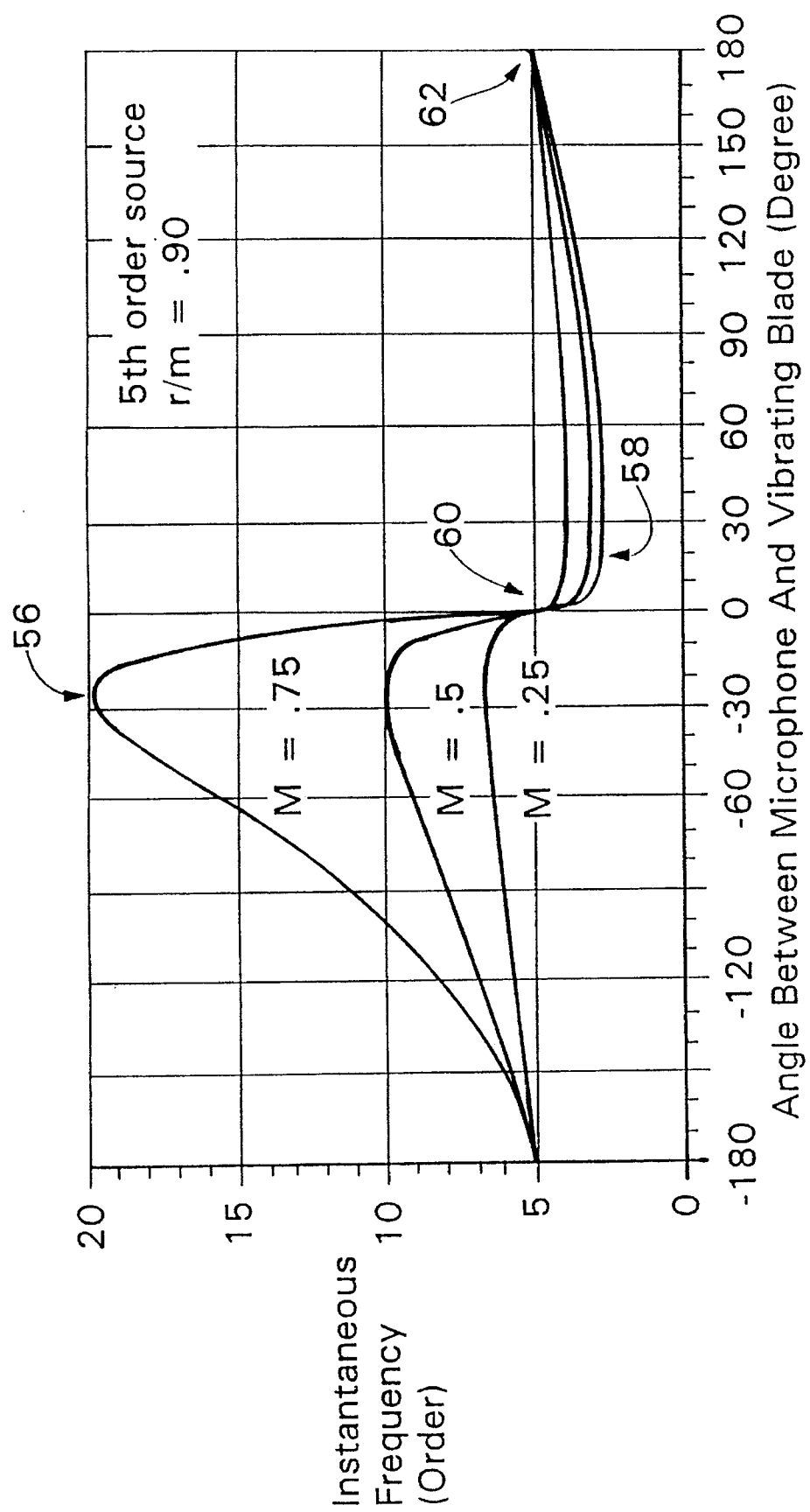

FIG. 9A
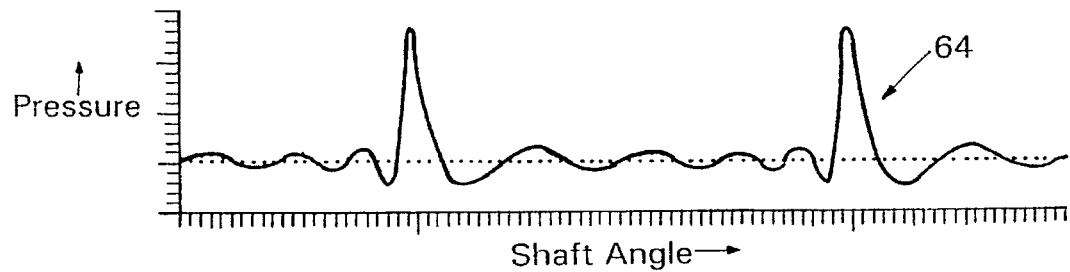
FIG. 9B
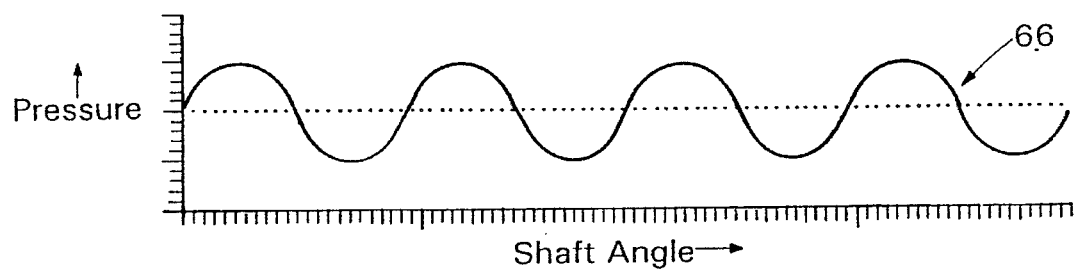
FIB. 9C
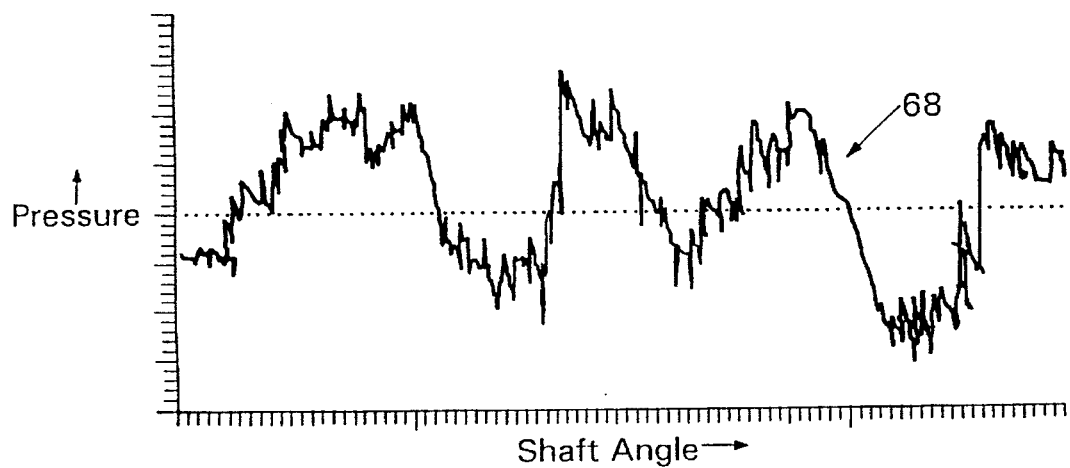

METHOD AND APPARATUS FOR ISOLATING AND IDENTIFYING PERIODIC DOPPLER SIGNALS IN A TURBINE

FILED OF THE INVENTION

The present invention relates to monitoring the vibration of turbine blades in an operating turbine and more particularly to a method and apparatus for detecting and locating resonantly vibrating turbine blades and their frequency of vibration from the acoustic signals radiated by the resonating blades.

BACKGROUND OF THE INVENTION

A rotating and resonating turbine blade radiates an acoustic signal which, when detected by a stationary acoustic sensor, can be characterized by a Doppler waveform. The characteristics of the detected acoustic signal are well understood. However, the characteristic Doppler signal is masked by other sounds generated by turbine operation. The present invention provides an improved means of isolating the characteristic Doppler signal from those signal components that mask the Doppler signal in order to identify the causal blade and its vibration frequency.

In U.S. Pat. No. 4,422,333 a method and apparatus for detecting and identifying one or more excessively vibrating turbine blades is disclosed. At the heart of the invention is the use of a pressure microphone as an acoustic sensor embedded in the stationary casing of the turbine for listening to the sound radiated by a vibrating and rotating blade. Methods of processing the acoustic sensor output signal to separate the desired characteristic Doppler waveform from random noise and periodic background sounds that accompany it were introduced.

In U.S. Pat. Nos. 4,996,880 and 5,152,172 improved methods for separating the desired characteristic Doppler signal from the accompanying periodic background based upon physical characteristics of a resonant blade and the small speed perturbations exhibited by all turbines including those run at "constant speed" are disclosed. Improved Hilbert Transform detection methods for identifying the position of any resonating blade and the frequency at which it vibrates and means and methods to detect and locate blades vibrating at frequencies other than harmonics of the machine rotational speed such as is encountered in aeroelastic blade flutter were also introduced, along with improved detection methods incorporating pairs of acoustic sensors. Methods of introducing deliberate torsional vibration to a turbine-generator train were disclosed to analyze the resulting blade vibration as a means of characterizing the turbine blading. Lastly, means to detect aerodynamic events including condensation shock, rotating stall in an operating turbine, differential nozzle wear, and order-related torsional vibration were introduced.

The U.S. Pat. No. 4,422,333 presented satisfactory methodology for acquiring an information-bearing acoustic signal at a fixed site reflecting the dynamics of the rotating turbine blading. It further presented a satisfactory means of suppressing the random flow noise components that mask the periodic Doppler signal characteristic of a vibrating blade. However, it failed to provide an effective means of separating the periodic Doppler from other periodic tones present in the turbine.

The U.S. Pat. Nos. 4,996,880 and 5,152,172 describe the first principles for effective separation of the characteristic Doppler from masking periodic tones. A process deriving a "difference Doppler" signal was introduced. However, the implementation is flawed in that excessive measurement time is required, only a small portion of the measured data is actually used in the final computation, and multiple and different "answers" are possible due to a required selection of the actual data subset employed. Additionally, the process employs an unnecessary number of transformations between the time and frequency domains, resulting in a loss of precision and an increase in computational time. The display resolution is limited by the initial sample rate employed in data acquisition, and producing output results with "point-per-blade" resolution is technically infeasible. Finally, the method prescribes retaining an unnecessarily large body of measured data, increasing the amount of hardware storage required.

SUMMARY OF THE INVENTION

Briefly stated, the present invention provides an apparatus for isolating from periodic background noise an acoustic signal characterizing the vibration of a resonantly vibrating turbine blade in a row of turbine blades secured to a rotating shaft from data acquired at more than two different operating shaft rotational speeds to identify the vibrating blade. In a first preferred embodiment, the apparatus comprises an acoustic sensor positioned on a stationary member with respect to the shaft to receive sound waves emanating from the rotating blades as the blades rotate about the rotor axis and to provide an acoustic signal from the received sound waves. The acoustic sensor is positioned with respect to the shaft so that the vibrating blade approaches and departs from the acoustic sensor in the course of one rotation of the shaft about the rotor axis. A reference means obtains a reference signal indicative of rotor position at least once each time the shaft completes a revolution about the rotor axis and determines the shaft speed. A sampling means samples the acoustic signal to obtain samples as a function of shaft position as the shaft completes a multiplicity of revolutions at a plurality of different shaft speeds. A first memory means temporarily stores the shaft speed from the reference means and a corresponding plurality of samples synchronized with the shaft position obtained by the sampling means. The plurality of samples together comprise a sample series representing at least one shaft rotation. An ensemble averager averages multiple sample series to develop a plurality of synchronous ensemble averages differentiated by shaft speed. A second memory means stores the plurality of synchronous ensemble averages segregated by shaft speed, and an accompanying shaft speed histogram. A Fourier decomposition means generates a plurality of complex order-normalized spectra segregated by shaft speed, from the stored synchronous ensemble averages, each complex order-normalized spectrum having a real component and an imaginary component. Curve fitter means curve fit the plurality of complex order-normalized spectra, using the shaft speed histogram as a weighting function, to generate a series of generally linear shaft speed functions fit to the real and imaginary Fourier coefficients of the complex order-normalized spectra. The Fourier slope coefficients represent a characteristic Doppler signal and the Fourier intercept coefficients represent the content of the periodic background noise. A synthesis means constructs the acoustic signal characterizing the vibration of the resonantly vibrating turbine blade and a Hilbert transform of the signal from the linear shaft speed functions generated by the curve fitter means. Lastly, a complex demodulation means determines the vector resultant of the constructed acoustic signal and its Hilbert transform, the peak of which identifies the resonantly vibrating blade and the relative amplitude of its vibration.

In a first alternate embodiment of the invention, the apparatus, using the same data acquisition means, and reference means as the prior embodiment, in conjunction with a sample control circuit, temporarily stores a plurality of samples of the data acquired in a first memory means. The plurality of samples together comprise a time history per blade revolution. A Fourier decomposition means generates a multiplicity of complex order-normalized spectra from the time history data reflecting the spectral content of a single most recently completed shaft revolution. A first ensemble averager means forms and accumulates an average complex order-normalized spectrum from the multiplicity of complex order-normalized spectra. An address deviation look-up table cooperating with the reference means generates an instantaneous speed deviation. A multiplier means multiplies the complex order-normalized spectrum and the instantaneous speed deviation to generate a multiplicity of speed weighted complex order-normalized spectra. A second ensemble averager means forms and accumulates an average speed weighted complex order-normalized spectrum from the speed weighted complex order-normalized spectrum. A deviation statistics module averages instantaneous shaft speed deviations to generate deviation statistics. Curve fitter means substantially simultaneously fit a linear function of the shaft speed deviation to the real and the imaginary components of the averaged complex order-normalized spectrum and the averaged speed weighted complex order-normalized spectrum using the deviation statistics, to generate a series of generally linear shaft speed functions. A synthesis means constructs an acoustic signal characterizing the vibration of the resonantly vibrating turbine blade and a Hilbert transform of the signal from the linear shaft speed functions generated by the curve fitter means. Lastly, a complex demodulation means determines the vector resultant of the constructed acoustic signal and its Hilbert transform, the peak of which identifies the resonantly vibrating blade and the relative amplitude of its vibration.

In a second alternate embodiment of the invention, the first memory means temporarily store a plurality of samples of the data acquired by the data acquisition means, wherein the plurality of samples together comprise an instantaneous angle history. A period detector circuit cooperates with a shaft speed deviation look-up table to generate an instantaneous speed deviation. Deviation statistics are generated by a deviation statistics module by averaging instantaneous speed deviations. A first ensemble averager means generates an average angle history from the instantaneous angle history. A multiplier means multiplies the instantaneous speed deviation and the instantaneous angle history to generate a speed weighted angle history. A second ensemble averager means generates an average speed weighted angle history from the speed weighted angle history. A first Fourier decomposition means generates an average complex order-normalized spectrum from the average angle history, and a second Fourier decomposition means generates an average speed weighted complex order-normalized spectrum from the average speed weighted angle history. The results are curve fit by a curve fitter means, which simultaneously fits a linear function of the shaft speed deviation to the real and the imaginary components of the averaged complex order-normalized spectrum and the averaged speed Weighted complex order-normalized spectrum using the deviation statistics, to generate a series of generally linear shaft speed functions. A synthesis means constructs an acoustic signal characterizing the vibration of the resonantly vibrating turbine blade and a Hilbert transform of the signal from the linear shaft speed functions generated by the curve fitter means. Lastly, a complex demodulation means determines the vector resultant of the constructed acoustic signal and its Hilbert transform, the peak of which identifies the resonantly vibrating blade and the relative amplitude of its vibration.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 8 is a graphic illustration of the frequency modulation component of three fifth order Doppler signals at differing blade tip Mach numbers;

FIGS. 9A, 9B, and 9C are graphical illustrations of the three constituents that sum to form the sound pressure waveform in a turbine casing;

DETAILED DESCRIPTION OF PREFERRED EMBODIMENTS

Figure 1:
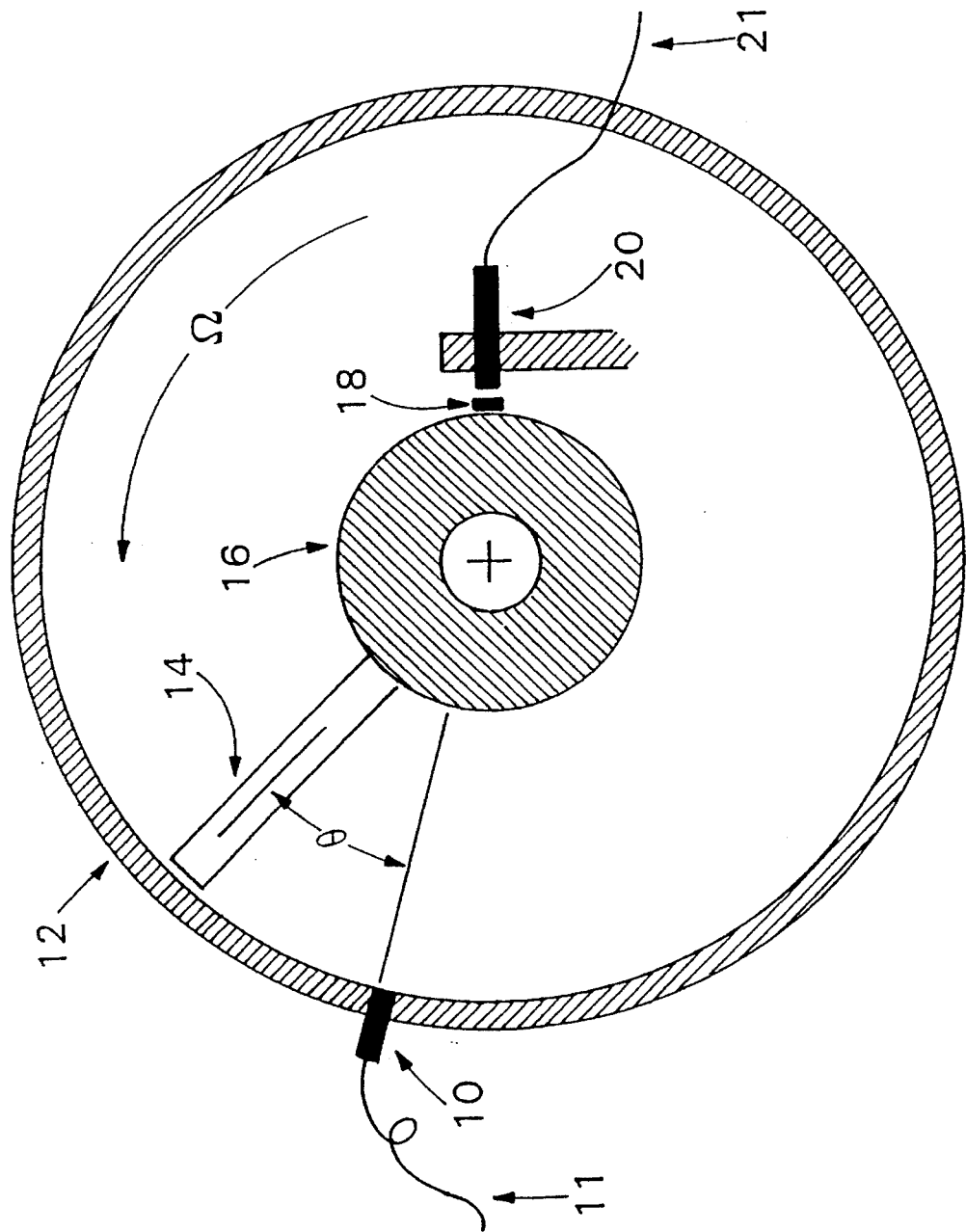
FIG. 1 is an axial cross-section schematic view of a portion of a turbine showing the relationship between a rotating blade, a sensing microphone and a reference tachometer.

The present invention provides a method and apparatus for isolating a characteristic Doppler signal of a resonantly vibrating blade from masking periodic and random noise. The present invention improves upon the apparatus and methods disclosed in U.S. Pat. Nos. 4,422,333, 4,996,880, 5,152,172, each of which are incorporated herein by reference, and provides a process leading to a "generalized difference Doppler" signal using substantially all available measured data, not merely the difference of two averages selected from a larger body of information. The outcome of the process is thus an unambiguous and unique answer. The new process is computationally efficient, requiring only one transformation from the time domain to the frequency domain and one from the frequency domain to the time domain. This is half the number of transformations between the time and frequency domains of the prior technology. The present invention provides hundreds of points per revolution in the characterizing resonant amplitude and resonant frequency functions spaced at desired angular intervals rather than at the fixed sixty-four points per revolution of the prior art. This "point-per-blade" resolution is accomplished without a corresponding burden on the measurement hardware. The "generalized difference Doppler" signal can be generated from two retained ensemble averages. In contrast, the prior art "difference Doppler" required a multiplicity of such ensembles, with sixteen being typical. The averages leading to the "generalized difference Doppler" signal can be computed in either the frequency or time domains. The prior "difference Doppler" method is restricted to time domain averaging exclusively.

The present invention includes apparatus and methods to evaluate both an information-bearing resonant signal and its Hilbert transform via direct synthesis with interpolating sample step-size and aligning phase offsets from the Fourier slope-coefficients that represent the first-difference approximation of the derivative of the synchronous ensemble average of a vibrating blade-produced acoustic signal with respect to the rotating speed of the shaft to which the blade is affixed. The Fourier slope coefficients are derived via curve-fitting applied to synchronously averaged and order-normalized spectral ensembles containing the real and imaginary Fourier coefficients of the acoustic signal and speed-weighted images thereof or speed segregated subsets thereof.

The present invention also provides a novel arrangement of components and processes that (1) perform synchronous ensemble averaging upon a sound pressure wave sensor produced signal embedded in a turbine casing, (2) perform order-normalized Fourier decomposition of this averaged data, (3) execute a curve-fit of a linear shaft-speed function to each resulting real and imaginary Fourier coefficient, and (4) use the resulting slope coefficients to synthesize an information-bearing analytic signal composed of a resonant signal and its Hilbert transform.

Referring now to the drawings, wherein like numerals indicate like elements throughout, FIG. 1 illustrates a schematic axial cross-section of a turbine, such as a steam turbine, showing transducer installations in accordance with a preferred embodiment of the present invention. A microphone or other sound pressure wave or acoustic sensor 10 is mounted in a stationary casing 12 of the turbine downstream of a selected blade row of the turbine rotor, and monitors the selected blade row. The blade row contains a plurality of rotating blades 14 affixed to and driving a central turbine shaft 16. A tachometer target 18 is affixed to the shaft 16 and is viewed by a tachometer probe 20. The microphone 10 produces an output signal along line 11 having a voltage proportional to the sound pressure within the turbine casing 12 at a location proximate to each blade 14 once per revolution. The tachometer probe 20 produces a once-per-revolution output logic signal 21 used to identify the angular position ($\theta$) of the shaft 16. The angular velocity of the blade is indicated by $\Omega$.

A resonating rotating blade 14 vibrates at an integer multiple of the turbine shaft 16 rotational frequency. This sympathetic vibration occurs when a "natural frequency" of the blading corresponds to a given multiple of shaft speed and represents the intersection of fundamental blade structural properties with harmonic forcing functions developed by the operating turbine. When such an intersection occurs, the blade 14 vibrates sinusoidally at the natural frequency with a characteristic "mode shape". That is, the motion of the blade 14 at a fixed time instant is spatially distributed in the mode shape. The motion at any single point is a sinusoidal function of time.

Figure 2A:
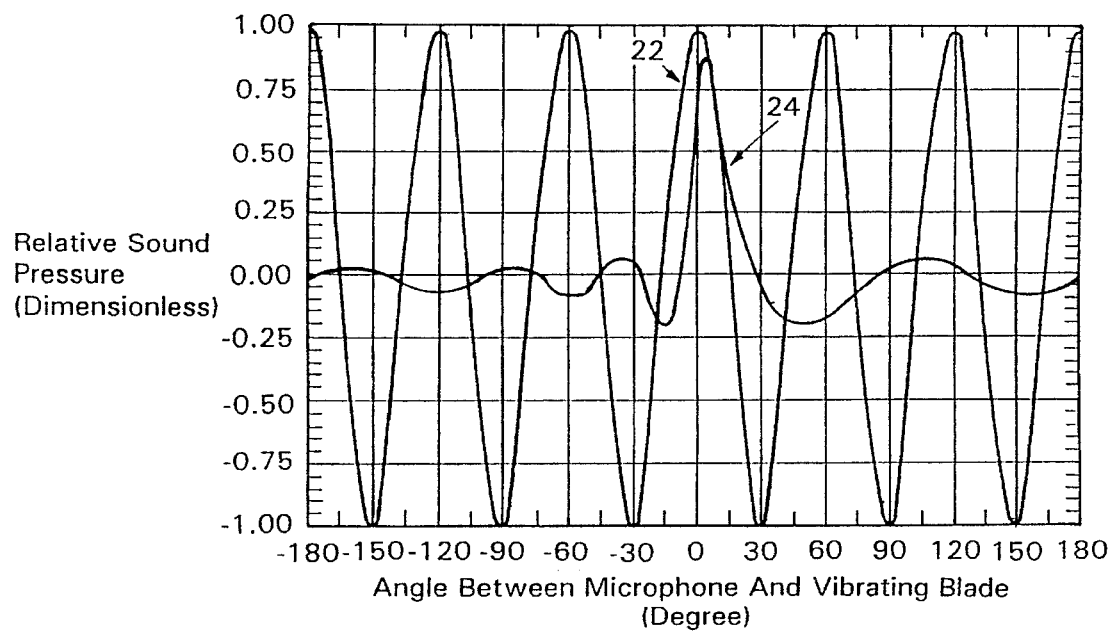
FIG. 2A is a graphic illustration depicting sound pressure waveforms caused by a vibrating blade as heard on the rotating blade and as heard by a non-rotating sensor.

FIG. 2 presents sound pressure fluctuations produced by a rotating row of turbine blades at two sites. When a blade 14 vibrates, it generates sinusoidal pressure fluctuations in the medium surrounding it. That is, it generates sound at the same frequency as the vibration. A microphone or other acoustic sensor rotating with the blade hears the produced sound with constant volume and pitch. In the present embodiment, a microphone 10 positioned at a fixed site in the turbine casing 12 monitoring the rotating blade 14 hears a different sound, one with rapidly increasing and decreasing volume and pitch. The microphone 10 hears an image of the radiated sound modified by the well known Doppler effect.

Figure 2B:
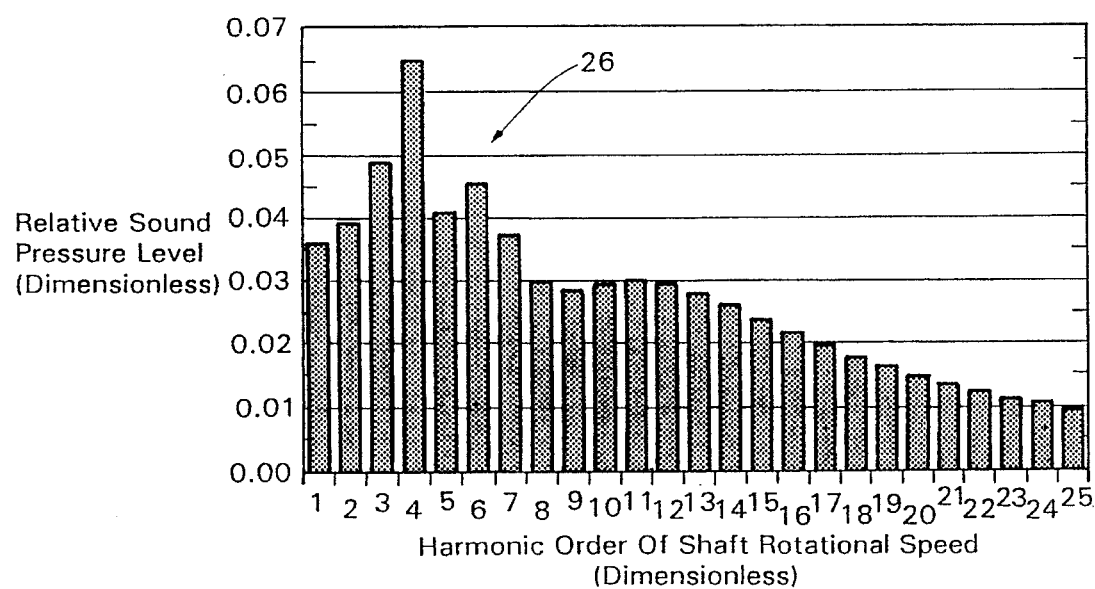
FIG. 2B is a graphic illustration of the spectrum of the sound at the non-rotating sensor.

The dotted trace 22 illustrates a sound close to a point near the tip of a rotating and resonating blade 14 (near field). The solid trace 24 illustrates the sound as heard by a microphone 10 at a fixed point in the turbine casing 12. This is the characteristic Doppler signal. Since the blade 14 generally rotates at an essentially constant speed, the horizontal angular axis presented also represents a time axis. The blade 14 is closest to the fixed point microphone 10 when the angle between the microphone 10 and the blade 14 is zero. The blade 14 is diametrically opposite to the fixed point microphone 10 at either horizontal extreme (±180°). The near field sound 22 has a spectrum with only one harmonic line (order 6, in this example). While the near field sound 22 is of a single frequency, the sound 24 heard at the remote and fixed microphone 10 is more complex. FIG. 2B presents the corresponding spectrum 26 of the sound 24 heard by the fixed point microphone 10. Note that the amplitude and frequency modulation caused by the Doppler effect spreads the energy of the signal from the microphone 10 across a broad range of harmonics. Note further, that the largest spectral amplitude does not occur at the frequency of the source.

Figure 3:
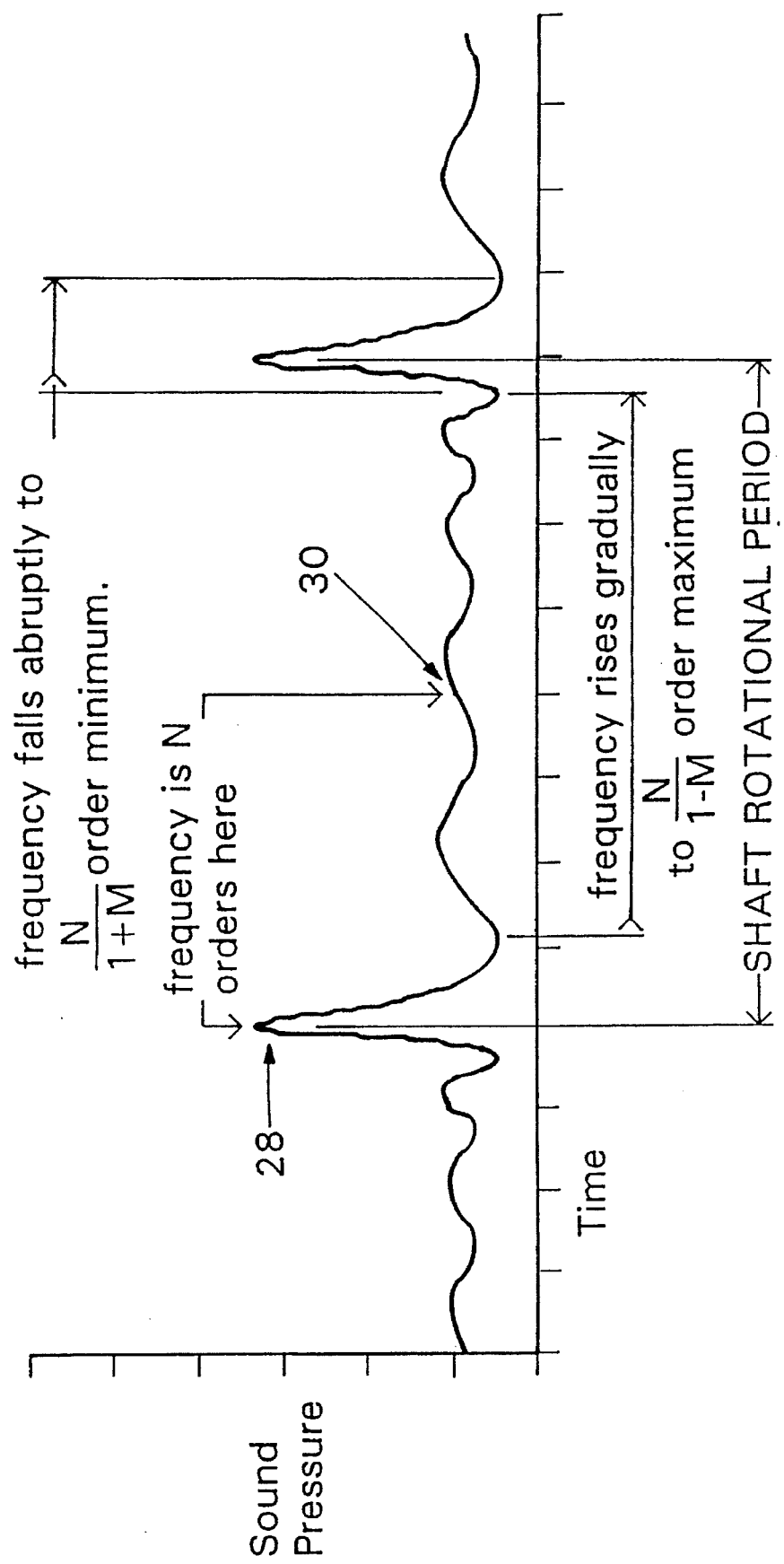
FIG. 3 is a graphic illustration of the characteristics of a Doppler waveform generated by a vibrating and rotating blade.

FIG. 3 details the changing characteristics of the characteristic Doppler signal generated by the fixed microphone 10 as the resonating blade 14 rotates past. The sound is loudest at location 28 where the blade 14 is nearest the microphone 10 and is quietest at location 30 where the vibrating blade 14 is diametrically opposite the microphone 10. At both of these locations 28, 30, the pitch frequency heard at the microphone 10 is identical to the frequency at which the blade 14 actually vibrates. This frequency is generally some integer multiple, N, of the shaft rotational speed. As the vibrating blade 14 approaches the microphone 10, the pitch heard by the microphone 10 increases gradually. The maximum frequency heard by the microphone 10 is determined by the vibration frequency and by the Mach number, M, of the tip of the rotating blade 14 (the tip Mach number is the tangential velocity of the blade tip divided by the speed of sound in the driving medium). A maximum pitch of N/(1–

M) times the shaft rotational frequency is attained. The angular location at which the maximum pitch occurs is determined by the radius of the microphone, m, and the radius of the sound source, r. When the approaching blade 14 makes an angle of $\cos^{-1}(r/m)$ with the microphone 10, the maximum pitch frequency is heard by the microphone 10.

Figure 4:
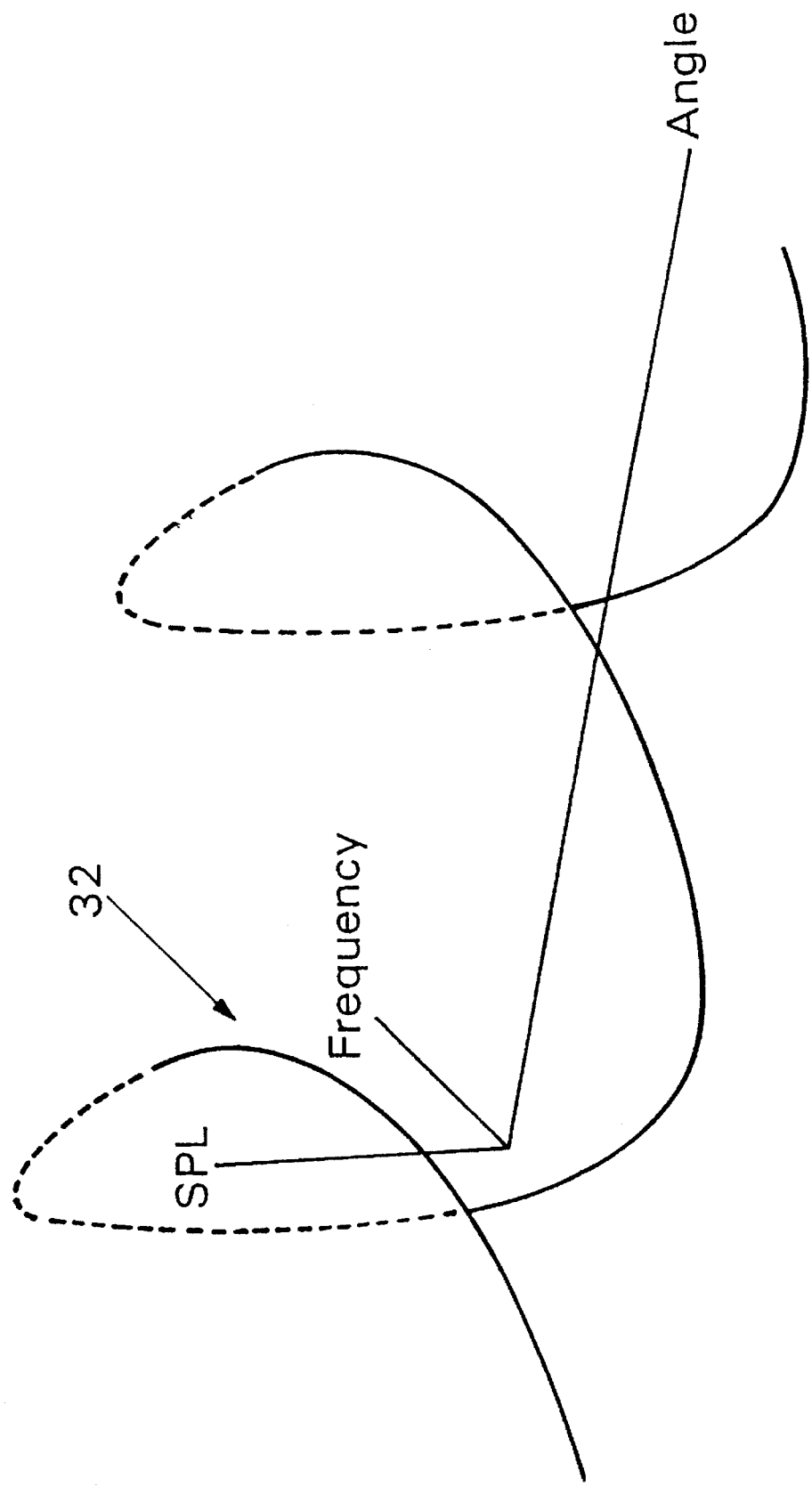
FIG. 4 is a three-dimensional graphic illustration of the pressure, frequency, shaft angle track of a vibrating blade Doppler signal.

The pitch frequency rises slowly to the maximum frequency. It then drops rapidly, reaching a minimum of $N/(1+M)$ times the shaft rotational frequency when the blade 14 is an angle of $\cos^{-1}(r/m)$ beyond the microphone 10. During this rapid frequency descent, the blade 14 passes the microphone 10. At this instant the microphone 10 hears a pitch that is exactly N times the shaft rotational frequency. The interaction of the sound pressure level (SPL), pitch frequency and blade angular position (or time) may be represented in three dimensions as shown by the trace 32 in FIG. 4. The aforementioned variations in volume and pitch repeat in every revolution of the turbine rotor. That is, the signal is periodic. Two dimensional projections of the pressure-frequency-angle trajectory provide valuable insight.

Figure 5:
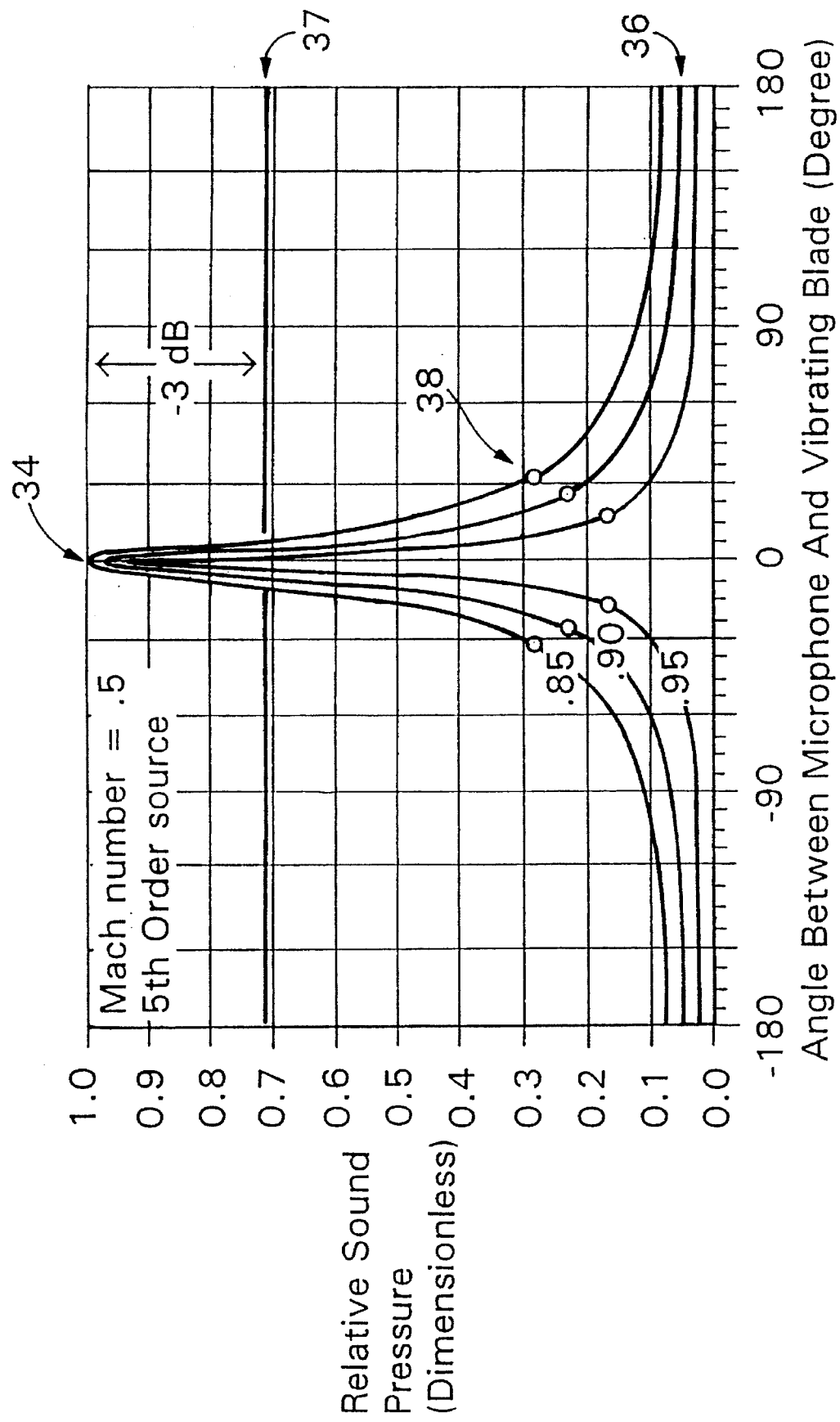
FIG. 5 is a graphic illustration of the amplitude modulation component of a Doppler signal for three different blade radius/microphone radius ratios.

FIG. 5 presents the pressure-versus-angle projection for three different values of the r/m ratio. FIG. 5 describes the amplitude modulation imposed upon the characteristic Doppler signal. It is noted that the r/m ratio, uniquely, controls the amount of amplitude modulation induced. While the Mach number, M, and source order, N, have been standardized in this figure, they have no influence on the shape of this projection. FIG. 5 has been normalized so that maximum sound pressure, indicated at 34, is equal to one. The corresponding minimum sound pressure, indicated at 36, occurs when the vibrating blade 14 is diametrically opposite the sensing microphone 10. The normalized minimum sound pressure 36 is numerically equal to $(m-r)/(m+r)$. The sound pressure is 70.7% of the maximum 34 (or −3 Db) at two blade locations symmetrically disposed about the microphone 10 an angle of $\pm\cos^{-1}(2-r/2m-m/2r)$, indicated at 37. At the characteristic $\cos^{-1}(r/m)$ angles 38 the sound pressure level is numerically equal to the square root of the minimum sound pressure level 36.

Figure 6:
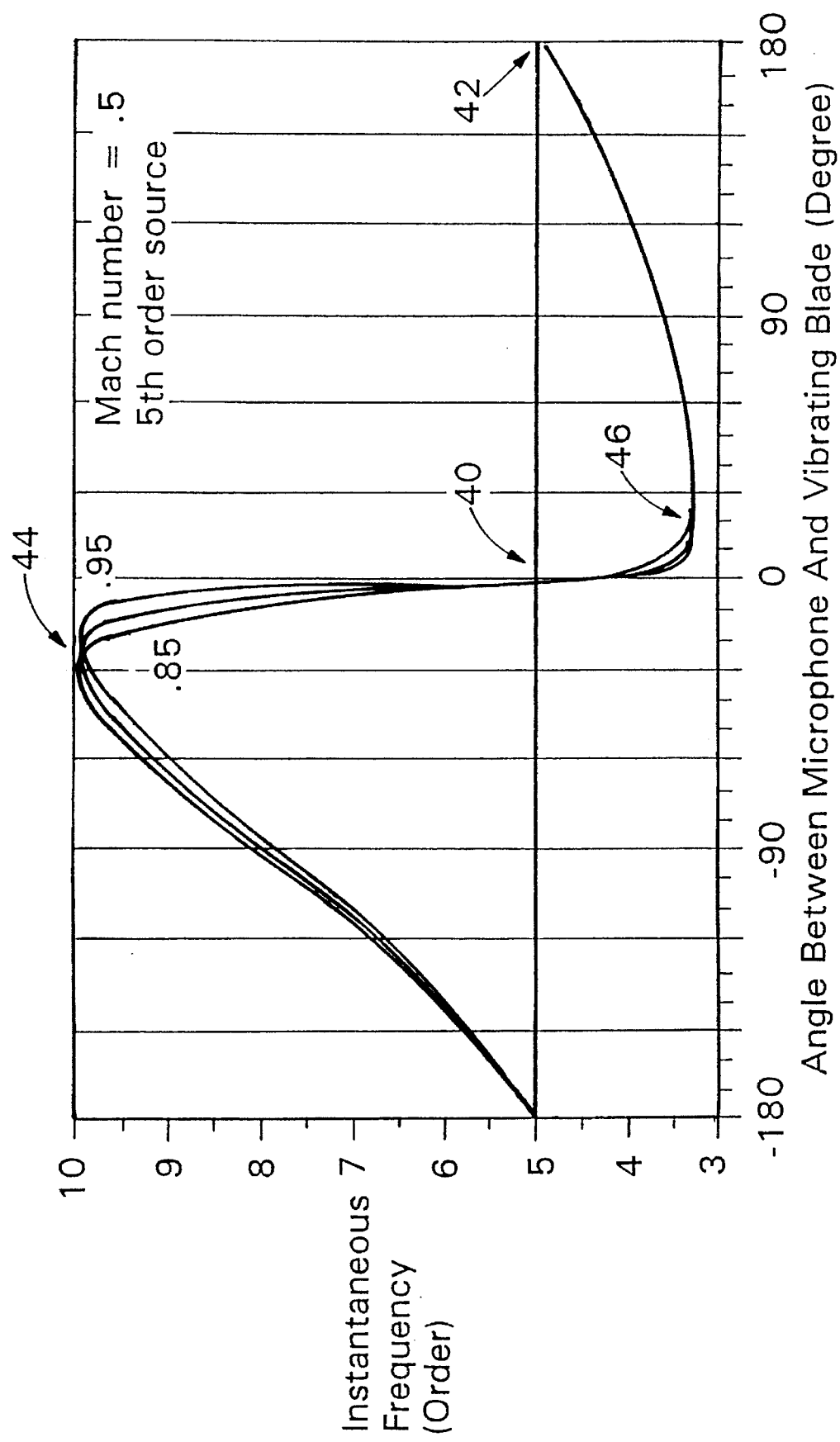
FIG. 6 is a graphic illustration of the frequency modulation component of a Doppler signal for the three different blade radius/microphone radius ratios of FIG. 5.

FIG. 6 presents the corresponding frequency-versus-angle projection. In this figure, three values of the r/m ratio are also presented. The Mach number, M, and the source order, N, have been standardized to the same values presented in FIG. 5. It is noted that both of these variables (M, N) influence the shape of this projection. The source frequency order, N, is heard when the blade 14 is adjacent the microphone 10, indicated at 40 and when it is diametrically opposite the microphone 10, indicated at 42. As previously discussed, maximum frequency, indicated at 44 perceived at the microphone 10 occurs when the approaching blade 14 is an angle of $\cos^{-1}(r/m)$ away. When the blade 14 has passed the microphone 10 and is moving away, a minimum frequency shown as point 46 is perceived when the blade 14 is an angle of $\cos^{-1}(r/m)$ beyond the microphone 10. Note further, that the extreme frequency bounds for the three traces presented are identical. Thus, the r/m ratio determines where the maximum and minimum frequencies occur but does not determine the value of these extremes.

Figure 7:
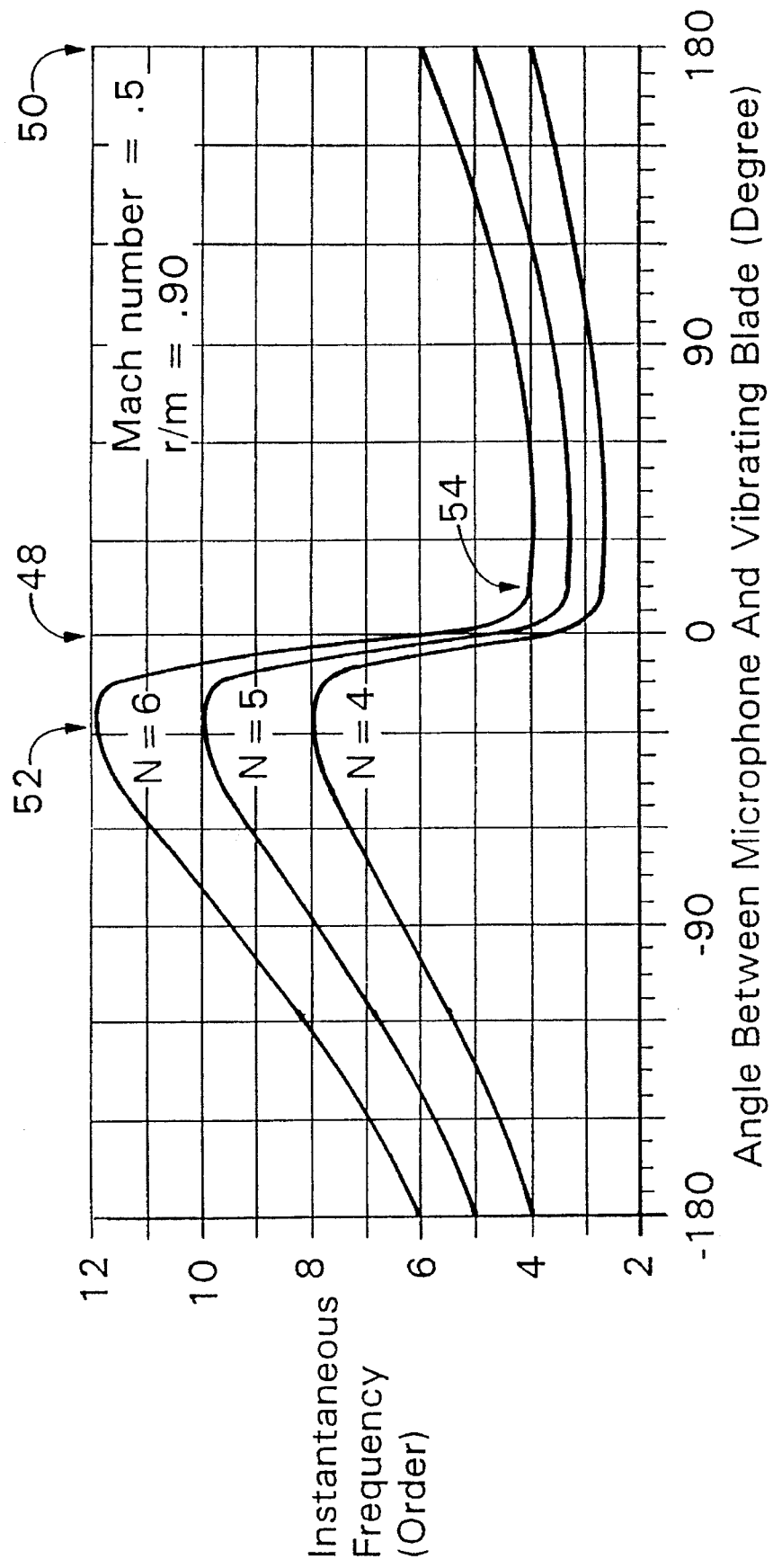
FIG. 7 is a graphic illustration of the frequency modulation component of three Doppler signals of different source frequencies.

FIG. 7 presents similar frequency-versus-angle projections for three different source frequency orders, N. Here, the r/m ratio and the Mach number, M, have been held constant. Note that the source order, N, is heard when the vibrating blade 14 is adjacent the microphone 10 shown at point 48, and when it is diametrically opposite, shown at point 50. A maximum frequency 52 of $N/(1-M)$ times the shaft rotational frequency is heard when the approaching blade 14 is at an angle of $\cos^{-1}(r/m)$ away. A minimum frequency, shown at point 54, of $N/(1+M)$ times the shaft rotational frequency is heard when the blade 14 is at an angle of $\cos^{-1}(r/m)$ beyond the microphone 10.

FIG. 8 shows the influence of the blade tip Mach number, M. In this frequency-versus-angle projection, the r/m ratio and the source frequency order, N, are held constant while functions of three values of blade tip Mach number are plotted. It is noted that an increase in source velocity (or a reduction in the speed of sound) has a profound change on the maximum frequency heard, shown at 56, and a less profound effect on the minimum tone pitch, shown at 58. It is further noted that the source order, N, is heard when the blade 14 is adjacent the microphone 10, denoted as 60, and diametrically opposed to the microphone 10, denoted as 62, regardless of the blade tip Mach number M.

FIGS. 9A, B and C illustrate the three distinct constituents of the sound signal heard by the microphone 10. The characteristic Doppler signal 64 is only present when a blade 14 experiences resonant vibration. The exact frequency match required to cause such sympathetic vibration may only last for a short period of time, hence, the Doppler signal 64 must be considered transitory. Further, to the contrary of the scales presented, the characteristic Doppler signal 64 is likely to be much smaller in amplitude than the other two constituents discussed below. The resonant frequencies most frequently sought are in the frequency range of five to ten times shaft speed, with resulting characteristic Doppler signal content spanning some twenty-five (25) orders of shaft speed. The periodic background noise 66 contains all manner of tonal sound components caused by the repetitious passage of asymmetries by the microphone 10. The most dominant of these tones is (normally) the group passage frequency, the number of banded blade packets comprising the monitored rotor stage multiplied by the shaft turning frequency. The group passage frequency is typically 30 to 50 orders of shaft rotational speed. Second and third harmonics of the group passage frequency compete with the blade passage frequency, a much higher tone equal to the number of blades in the monitored rotor stage multiplied by the shaft turning frequency, as the second loudest tone. Various event-passage interactions lead to a rich content of low order shaft speed harmonics below the group passage frequency.

The random noise component 68 is the "shissing" sound produced by steam flow past the turbine blades. This component 68 normally dominates any time domain display of the microphone output signal on line 11, obscuring the periodic components 64 and 66 altogether. The random noise 68 is generally characterized by a "1/f" spectrum shape (f=frequency) well below the blade and group passage frequency root mean square (RMS) levels when the output signal is viewed in the frequency domain. Isolating the characteristic Doppler signal 64 from the remainder of the total output signal is a multi-step process.

The techniques described and implemented herein may be performed through the use of microprocessors and microcomputers which execute software packages implementing the algorithms further described hereinafter. Computer programs are known and currently available which provide for averaging, digital filtering, Fourier transformation, and correlation techniques. These programs and procedures are applicable to nonperiodic or irregular waveforms, such as the random noise component 68.

Isolating the desired characteristic Doppler signal 64 from the periodic background noise 66 is a more difficult matter. Both are periodic and they share similar bandwidths. The unwanted masking tones are normally larger than any single tonal component in the desired Doppler signal 64. Signal content at any order of shaft speed must be presumed to be a combination of both the characteristic Doppler signal 64 and the periodic background noise 66.

Figure 10A:
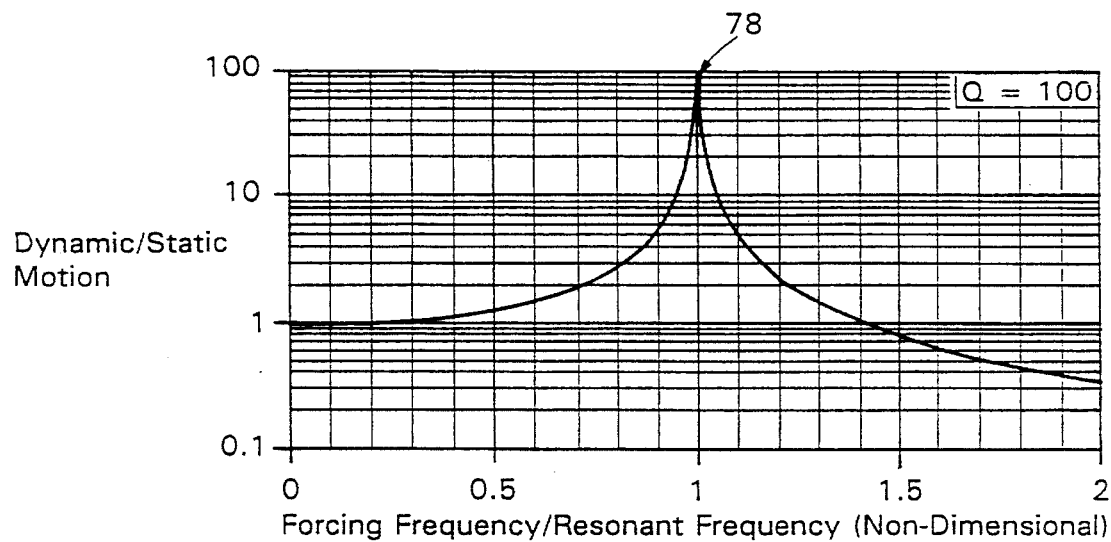
FIG. 10A is a graphic illustration of the magnitude characteristics of a "high Q" resonant structure.
Figure 10B:
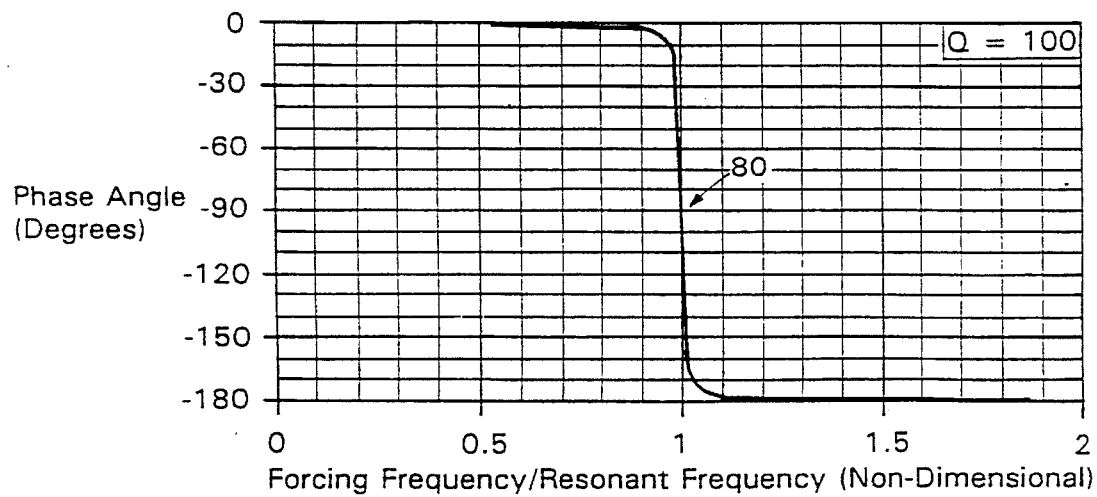
FIG. 10B is a graphic illustration of the phase characteristics of a "high Q" resonant structure.

FIGS. 10A and 10B present the first principal for differentiating between these overlapping periodic signals 64, 66. The characteristic Doppler signal 64 results from the (near) coincidence of a blade, group or rotor resonant frequency, $f_n$, with a driving harmonic of shaft rotational speed. The single frequency vibration of the blade 14 that results follows the response patterns illustrated. Turbine rotors are composed of tightly fitted metallic parts. Such assemblies exhibit minimal damping, the energy dissipating mechanism that tends to suppress vibrational response. Structures of this nature are said to exhibit "high Q" modes of vibration. Q is termed a "quality factor", a measure of damping numerically equal to the reciprocal of twice the non-dimensional viscous damping factor. Structures with very light damping are normally characterized by this parameter. Testing experience with real turbine blades indicate modal Q's in the range of 100 to 400 to be typical. The trace in FIG. 10A shows the displacement amplification of forced motion as a function of frequency for a structure with a Q of 100. At $f_n$, the resonant frequency maximum motion per unit of applied force is found at point 78. The response at resonance is Q times as great as the displacement resulting from the application of a static load of the same force. That frequency span, centered about the resonant frequency, over which the structure exhibits a gain of 0.707 Q or more is termed the "−3 Db bandwidth". The −3 Db bandwidth is numerically equal to the natural frequency, $f_n$, divided by Q. Thus, a high Q resonance can only be excited by a narrow range of frequencies. When resonance is excited, the response motion is significant.

The trace of FIG. 10B presents the associated force-to-displacement phase as a function of forcing frequency. At frequencies well below the blade resonance frequency, the response motion is in phase coincidence with the driving force. At frequencies well above the blade resonance frequency, the motion is in phase opposition to the causing force. In the narrow frequency range spanning the blade resonance frequency, the phase angle changes abruptly. Across the −3 Db bandwidth, the structure exhibits a phase change of 90°, providing an average phase slope of $-90\,Q/f_n$ (degree/Hertz). At exactly the resonant frequency, shown at 80, the phase is steepest, attaining a value of $-360\,Q/\pi f_n \approx -114.59\,Q/f_n$. This steep phase slope at resonance is the physical signal characteristic that differentiates the Doppler signal 64 from the masking periodic background noise 66. When the Nth harmonic of shaft rotational speed falls within the −3 Db bandwidth of a mode at natural frequency, $f_n$, resonant response at the resonant frequency results. Any small variation in the turbine's running speed results in modulating the phase relationship of this "carrier frequency" in proportion to the phase slope at resonance and to the speed variation exhibited by the turbine.

While power generation turbines are intended to run at "constant speed" (1800 or 3600 RPM in generating 60 Hz power, 1500 or 3000 RPM for 50 Hz power) the control mechanisms are imperfect. In a long-term sense, a power turbine runs at very precise speed with errors on the order of a few degrees per day being typical of U.S. operation. In a short term sense, the error is larger. Instantaneous speed error of ±1 RPM (±0.056%) can be found in any given rotation of an 1800 RPM generating system. If a power generation systems operates at a shaft speed of $(1\pm\Delta)f_0$, a mode resonant with the Nth harmonic experiences excitation over the frequency range $\pm N\Delta f_0$ resulting in a phase modulation of ±90 QΔ degrees, regardless of the order, N. Hence, all periodic components of the characteristic Doppler signal 64 are phase modulated as a function of machine speed. This phase modulation is in addition to the frequency and amplitude modulation imparted by the Doppler effect and is a basis upon which the characteristic Doppler signal 64 can be isolated from the periodic background noise 66.

The tonal periodic background noise 66 reflects harmonic pressure fluctuations due to the repetitive passing of flow obstructions such as blades and groups of blades past fixed nozzles. These noise producing mechanisms are not related to structural resonances and, hence, lack the steep phase slope(s) indicated at 80 associated with a resonating blade 14. Instead, these periodic components 66 exhibit an essentially fixed phase relationship over the small speed variations present in real machines.

FIGS. 11–14 are schematic block diagrams illustrating varying processes for isolating the characteristic Doppler signal 64 from the random and periodic background noise 66, 68 heard by a stationary microphone 10. The diagrams are meant to show the flow of data, beginning with analog data at a microphone as the data is put through various transformations. As such, the lines between and connecting various blocks do not specifically represent a hardware wire or line over which a signal travels, but may represent the transformation of data as it passes through a particular block, or from one block to another. Additionally, each block does not necessarily represent a particular hardware apparatus suited only for a particular purpose, but rather the blocks represent a step in the process of transforming the data from one form or format to another.

Figure 11:
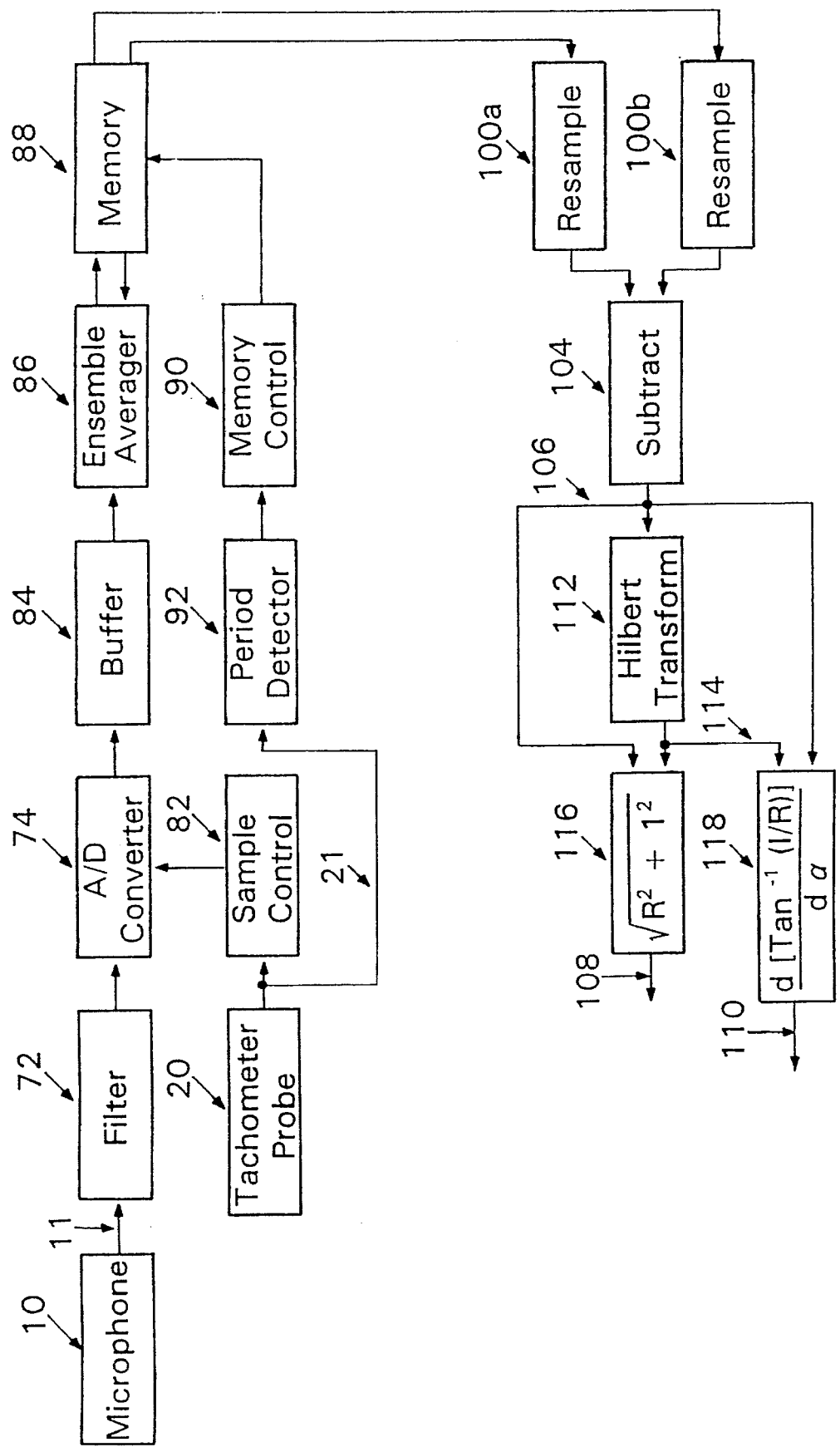
FIG. 11 is a schematic block diagram of a prior-art resonant blade detection and identification apparatus.

FIG. 11 is a schematic block diagram of a prior art method and apparatus showing the process of isolating the characteristic Doppler signal 64 from the random background noise 68. First, the microphone signal, shown along line 11 can be band-limited by use of a low pass filter 72. This filter 72 also serves as an "anti-aliasing" filter, allowing the microphone signal to be synchronously sampled by an analog-to-digital converter 74 without ambiguity of signal frequency content. Such low pass filtering can eliminate the blade passage frequency components and (for most geometries) the group passage frequency while still passing the twenty-five (25) orders desired from the characteristic Doppler signal 64. Hence the periodic background noise 66 is typically composed of harmonics similar to those of the characteristic Doppler signal 64 in order. The random noise 68 is discriminated against by employing "synchronous ensemble averaging" as originally proposed in U.S. Pat. No. 4,996,880. In ensemble averaging, successive sets of data (arrays) are collected and summed point by point as an array in a computer memory. After collection and summation are complete, the data are averaged by dividing the sum for each point by the number of scans performed. Ensemble averaging is effective in filtering out random noise, because the signal-to-noise ratio increases by the square root of the number of times the data points are collected and averaged. The advantage of ensemble averaging is realized by measuring points at a frequency that is at least twice as great as the highest frequency component of the waveform. Greater sampling frequencies provide no additional information, and include more noise. Here, the tachometer probe signal on line 21 is used as a means of process synchronization. The microphone signal is converted to a sequence of digital samples which is broken into a series of shorter sequences, each spanning one revolution of the shaft 16. These shorter sequences are aligned relative to a starting tachometer pulse and samples at like angular positions are summed together and divided by the number of revolutions sampled. This results in a record spanning one revolution with the same sample spacing as the original digital sequence. Because the random noise component 68 has no coherent relationship to the tachometer probe signal, it is averaged toward zero by this synchronous process. For practical purposes, only the periodic components 64 and 66 are reinforced, and so, remain.

The converter 74 acquires samples at a fixed sample rate. The sample rate in this embodiment corresponds to sixty-four samples per revolution at the nominal ($f_0$) operating speed of the turbine, although it should be apparent to those skilled in the art, that other sample rates may be chosen, and thus, the invention should not be limited to a method or apparatus sampling at sixty-four samples per revolution. The sampling is synchronized by a sample control circuit 82 so that the first of the sixty-four samples is acquired in coincidence with the arrival of the tachometer target 18 at the tachometer probe 20. A buffer of first memory means 84 retains the samples reflecting the pressure variation during the most recent single revolution of the shaft 16, starting from the arrival of the target 18 at the tachometer 20.

The data stored in the buffer 84 becomes one constituent in one of a plurality of ensemble averages retained in a processing or second memory means 88. Each of the ensemble averages retained in the memory 88 is associated with a specific shaft speed within the normal $(1\pm\Delta)f_0$ operating range, i.e., the ensemble averages stored in the memory 88 are speed segregated. A memory control circuit 90 determines which specific ensemble in memory 88 is to be augmented with the data stored in the buffer 84. This determination is made based upon the period of the revolution of the data retained in the buffer 84. The period of the revolution is measured by a period detector 92, which measures the number of clock pulses that arrive between adjacent pulses from the tachometer probe 20. In the presently preferred embodiment, the period is measured to a precision of 50 Ns by the period detector 92, and the tachometer probe 20 pulses at 20 Mhz.

The selected ensemble in memory 88 is used as one input to an ensemble averager 86 by the memory control 90. The ensemble averager 86 functions to add the data of buffer 84 to the selected ensemble returned from memory 88. This addition is done on a sample-by-sample basis, so that a sixty-four point result is produced in the same temporal format as the data of buffer 84. The augmented ensemble average is then returned to memory 88.

A shaft speed histogram is also maintained in the memory 88 and is used by the memory control circuit 90 to determine an address or location in the memory 88 at which to store the ensemble average just augmented. The histogram has one point or address for each ensemble average retained over the $(1\pm\Delta)f_0$ speed range. The memory control circuit 90 increments the point or address in the shaft speed histogram which corresponds to the shaft speed of the ensemble average just augmented. The act of incrementing the point in the histogram corresponding to the address simply counts the number of revolutions encountered and processed at the most recent revolution's exact shaft speed.

The microphone output signal is sampled and processed in "real-time" so that every revolution of the shaft 16 that occurs within the observation interval is characterized by period and provides an ensemble average constituent. The actions just described are repeated over a pre-defined observation interval, typically 30 minutes. At the end of this observation interval, the memory control circuit 90 shifts its attention to a physically different but functionally identical memory (not shown) so that the data stored in the memory 88 may be further processed while new information is continuously acquired. The memory 88 thus reflects tens of thousands of revolutions. The synchronous nature of the averaging discriminates against the random noise content 68 of the microphone signal. As previously discussed, the random noise 68 is diminished in proportion to the square root of the number of revolutions averaged. For practical purposes, the resulting plurality of ensembles represent only periodic information content. In the absence of any resonating blade 14, the form of each retained ensemble average would be identical (within statistically predictable limits based upon the number of revolutions captured in each ensemble). While the periodic background noise 66 is represented with identical amplitude-by-time form in each such ensemble, the appearance of a vibrating blade characteristic Doppler signal 64 varies between the ensembles as the act of discriminating by shaft rotational speed serves to demodulate the phase modulation imposed by the interaction of machine speed variation with a "high Q" resonance.

The distribution of this information by speed is contained in the shaft speed histogram which tends toward the Gaussian in shape with variations in mean and standard deviation over the course of an operating day. The shaft speed histogram is used to select two of the speed-segregated ensemble averages for further processing. The algorithm for this selection is to maximize the product of three terms: the revolution counts associated with a higher speed ensemble, the revolution counts associated with the lower speed ensemble and the difference in speed between the two ensembles. This serves to select two ensembles, each with a high degree of statistical confidence, that are most apt to reflect considerable difference in waveform shape due to a resonating blade 14. Each of the selected ensemble averages is subjected to a resampling process with the object being to produce two sixty-four point records sampled on a constant shaft angle increment rather than a constant time increment basis. Recall that the analog-to-digital converter 74 is clocked at a constant sample frequency numerically equal to sixty-four $f_0$. Sixty-four such samples taken when the shaft rotates at $(1\pm\Delta)f_0$ spans (very slightly) less then one revolution. Sixty-four samples taken when the shaft rotates at $(1\pm\Delta)f_0$ spans (very slightly) more then one revolution. The resampling process constructs a new sequence of sixty-four sample points that exactly span one revolution so that the two ensembles selected now have samples at exactly corresponding shaft angle positions. This resampling is accomplished by mapping the ensemble average from the time domain to the frequency domain by use of a co-location curve fitting process, in this example, using a resampling circuit 100a, 100b and knowledge of the exact shaft rotational speed associated with the ensemble chosen. This amounts to curve-fitting a sequence of (very slightly) over and/or under sampled sine and cosine waves to the ensemble. The resulting Fourier-like coefficients are then used to synthesize a new time domain function sampled at the desired sixty-four points. The two resampled ensembles are subjected to a point-by-point subtraction process by subtractor 104. Each of the sixty-four sample points from the higher shaft speed ensemble is subtracted from the corresponding point in the lower speed ensemble. The amplitude of the resulting sixty-four point difference is adjusted by dividing by a number proportional to the difference in shaft speed of the two ensembles. The resulting sixty-four point array is termed a "Resonant Signal" and is subjected to further processing. The Resonant Signal, indicated as 106, is the isolated approximation of the ideal Doppler signal 24 illustrated in FIG. 2A. It may be recognized as an approximation of the first derivative of the synchronous ensemble average of the monitored acoustic signal with respect to speed of the turbine. The Resonant Signal 106 contains the information necessary to determine which blade 14 (or blades) in a monitored blade row vibrates and the rotational order to which that blade 14 is responding sympathetically. This is accomplished by complex demodulation of the Resonant Signal 106 which returns the identified approximations of the pressure-versus-angle projection of FIG. 5 and the frequency-versus-angle projection of FIG. 6. These are termed the Resonant Amplitude 108 and Resonant Frequency 110, respectively.

The first step in the complex demodulation is to subject the Resonant Signal 106 to Hilbert transformation, shown in block 112, resulting in a new sixty-four point time history of different detailed shape but related informational shape. This transformation may be accomplished as a convolution in the shaft angle (time) domain. It may also be accomplished by applying a Fourier transformation to the Resonant Signal 106, phase shifting the resulting complex coefficients by 90° and applying an inverse Fourier transformation. Since the data of the Resonant Signal 106 is sampled exactly sixty-four times in the one revolution, an unweighted Fourier transformation may be employed. Given the data record of the Resonant Signal 106 is retained as a binary number of samples, any of the simplest fast Fourier transform (FFT) algorithms may be employed for this purpose. The Resonant Signal 106 is treated as the real component of a complex shaft angle (time) domain function. Its Hilbert transform, indicated at line 114 is treated as the imaginary component of this same function. The desired Resonant Amplitude 108 is derived by computing the vector resultant of the two complex constituents 106 and 114 on a point-by-point basis. This is accomplished by a magnitude resolver, shown at block 116. The required Resonant Frequency 110 is also resolved from complex components 106 and 114 on a point-by-point basis by a frequency resolver, shown at block 118. This resolution is accomplished by computing the arctangent of the quotient of the Hilbert transform 114 divided by the Resonant Signal 106 and then differentiating the resulting angle with respect to the shaft angle (time).

Figure 12:
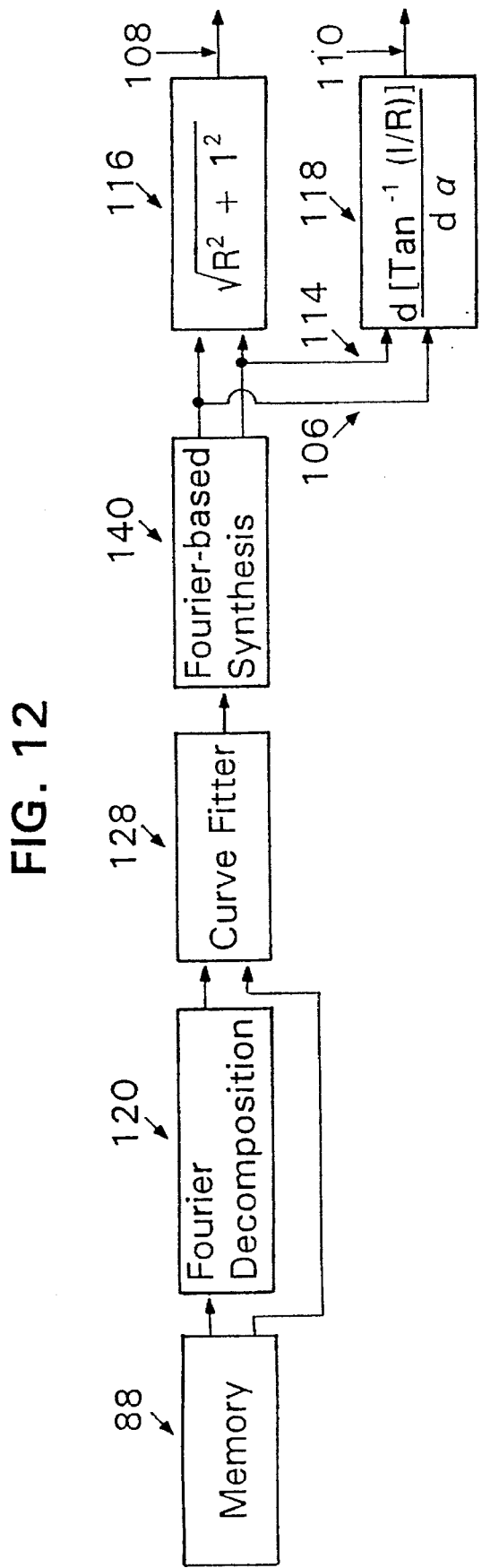
FIG. 12 is a schematic block diagram of a portion of one embodiment of the present invention.
Figure 13:
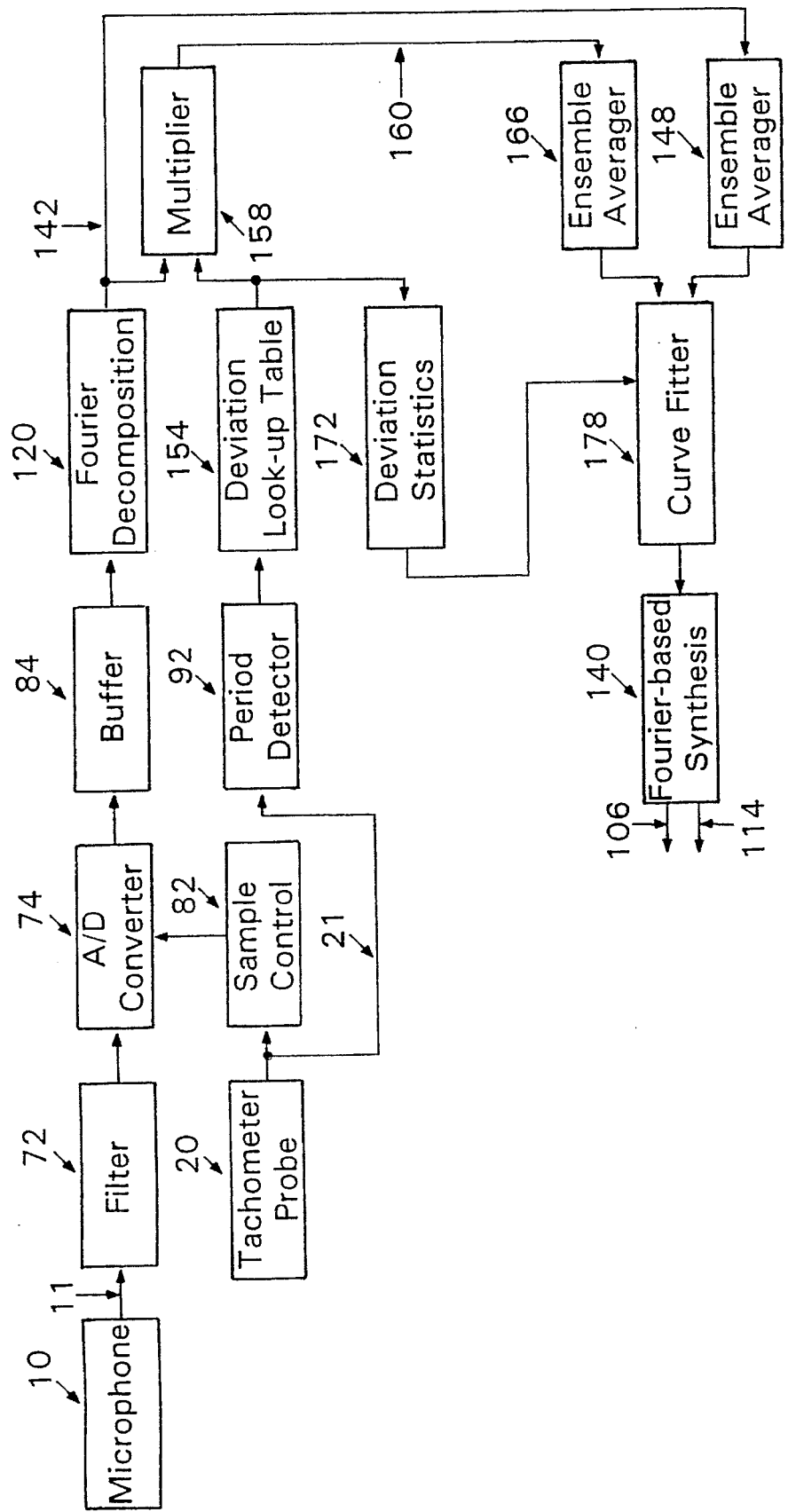
FIG. 13 is a schematic block diagram of a first alternate embodiment of the present invention.
Figure 14:
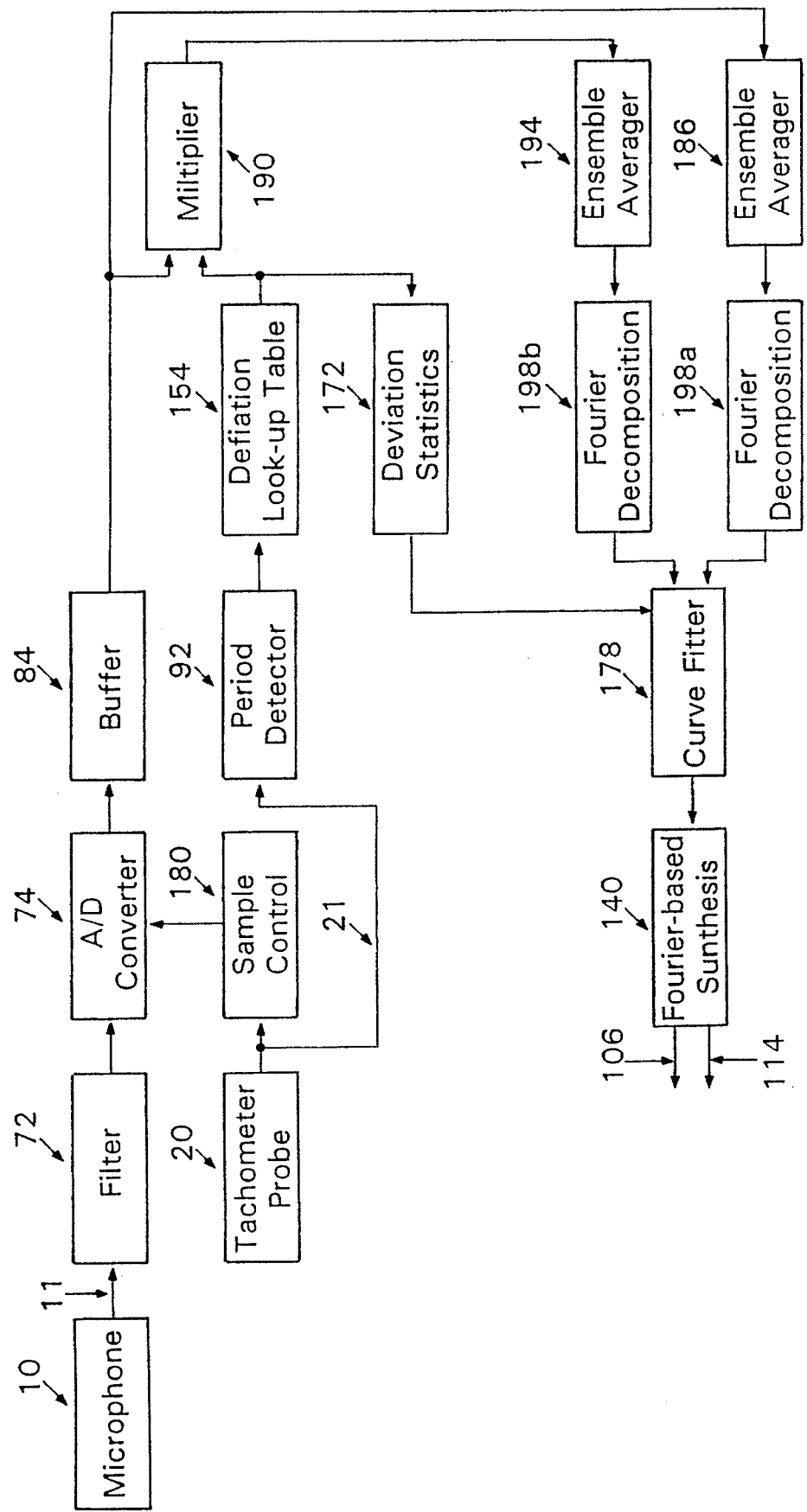
FIG. 14 is a schematic block diagram of a second alternate embodiment of the present invention.

FIGS. 12–14 disclose improved means and methods to isolate the Resonant Signal 106 and its Hilbert transform 114, including means to obtain "point-per-blade" resolution without need for revised sampling and storage hardware.

FIG. 12 illustrates a first preferred embodiment of the present invention, an improved means to obtain the desired signals 106 and 114. The process uses the plurality of synchronous ensemble averages segregated by shaft speed and the accompanying shaft speed histogram, previously discussed and shown in FIG. 11. The key feature of this method is that it uses all of the acquired ensemble averages, not just two of them. The process requires no selection of a data sub-set and has only one possible answer, thus eliminating any questions of interpretation.

The process commences by performing a Fourier decomposition, shown at block 120, upon each of the ensemble averages retained in the memory 88. The Fourier decomposition 120 cannot be a simple unweighted FFT because some of the ensembles are (very slightly) under-sampled while others are (very slightly) over-sampled from a nominal sixty-four samples per revolution. Instead, a co-location curve fitter and knowledge of the exact shaft rotational speed associated with each ensemble (from the shaft speed histogram) are employed. An harmonic series of thirty-one (very slightly) over and/or under sampled sine and cosine waves plus a mean (DC) value are curve fit to each ensemble. This results in a corresponding number of order-normalized spectra, one for each shaft rotational speed segregated in the original set of ensemble averages and counted in the shaft speed histogram. Each resulting order-normalized spectrum contains a real and an imaginary component array. Each array has thirty-one components representing the amplitudes of harmonically related cosine and sine waves, respectively. Each spectral array covers thirty-one orders (multiples) of shaft rotation with a resolution of one order. One order-normalized spectrum is obtained for each shaft rotational speed segregated in the original ensemble averages. In the absence of any resonantly vibrating blade 14, all of these spectra would be identical (within statistically predictable limits based upon the number of revolutions reflected by each spectrum). A resonating blade 14 (or blades) introduces spectral terms that differ with shaft rotational speed in a deterministic manner. Owing to the extremely small perturbations in shaft speed involved, these deterministic changes can be well modeled as linear changes in the amplitude of the real and imaginary component of each harmonic order as a function of shaft speed. Such a model is formed by numeric curve-fitting across all of the order normalized spectra.

The plurality of order-normalized spectra are subjected to a linear curve-fitter, shown at block 128, which also uses the shaft speed histogram as a weighting function input. The outcome of this process is a series of sixty-two linear shaft-speed functions fit to the real and imaginary Fourier coefficients of the order normalized spectra. There are thirty-one real (cosine amplitude) functions and thirty-one imaginary (sine amplitude) functions, each representing a distinct integer harmonic of shaft speed. Each such function is defined by a slope and an intercept (not shown). Curve-fitter 128 fits a linear function to each of the thirty-one real components in accordance with equation (1) below:

$$A_{in} = \Omega_n i + \omega_n \tag{1}$$

where $A_{in}$=the cosine coefficient for the nth order term of the ith speed average;

$\Omega_n$=a slope of a best fit straight line through the $A_{in}$ data points;

$\omega_n$=an intercept of the straight line;

i=an index to the shaft speed histogram, wherein ($0 \leq i \leq I$), and I=the number of shaft speed categories segregated during data acquisition; and n=a harmonic order number ($1 \leq n \leq N$), N=the maximum harmonic order decomposed.

This is accomplished by forming a "weighted squared error" and seeking its minimization. In this instance, the revolution counts of the shaft speed histogram are used as the weighting function. This weighting forces the fit to be biased toward speeds at which a large number of revolutions were accumulated. The line fit must be "tight" here. At speeds where fewer revolutions were acquired, the fit is allowed to be "looser". The method of solution is traditional. The weighted squared error is minimized by selecting slope, $\Omega_n$, and intercept, $\omega_n$, values that satisfy equations (2) and (3) simultaneously.

$$\frac{d\left\{\sum_{i=0}^{I}[C_i(\Omega_n i+\omega_n-A_{in})^2]\right\}}{d\Omega_n}=\phi \qquad (2)$$

where $C_i$=the revolution count in the ith speed segregation sample of the shaft speed histogram.

$$\frac{d\left\{\sum_{i=0}^{I}[C_i(\Omega_n i+\omega_n-A_{in})^2]\right\}}{d\omega_n}=\phi \qquad (3)$$

The solution to these simultaneous equations is provided by equations (4) and (5), following.

$$\Omega_n=\frac{\sum_{i=0}^{I}C_i\sum_{i=0}^{I}iC_iA_{in}-\sum_{i=0}^{I}iC_i\sum_{i=0}^{I}C_iA_{in}}{\sum_{i=0}^{I}C_i\sum_{i=0}^{I}i^2C_i-\left(\sum_{i=0}^{I}iC_i\right)^2} \qquad (4)$$

$$\omega_n=\frac{\sum_{i=0}^{I}i^2C_i\sum_{i=0}^{I}C_iA_{in}-\sum_{i=0}^{I}iC_i\sum_{i=0}^{I}iC_iA_{in}}{\sum_{i=0}^{I}C_i\sum_{i=0}^{I}i^2C_i-\left(\sum_{i=0}^{I}iC_i\right)^2} \qquad (5)$$

Simultaneous with the just described actions, curve-fitter 128 also fits a linear function to each of the thirty-one imaginary components in accordance with equation (6) below:

$$B_{in}=\Delta_n i+\delta_n \qquad (6)$$

where $B_{in}$=a sine coefficient for the nth order term of the ith speed average;

$\Delta_n$=a slope of a "best fit" straight line through the $B_{in}$ data points;

$\delta_n$=an intercept of the straight line;

i=an index to the shaft speed histogram, wherein ($0 \leq i \leq I$), and I=the number of shaft speed categories segregated during data acquisition; and n=a harmonic order number ($1 \leq n \leq N$), N=the maximum harmonic order decomposed.

The method of solution is exactly the same as employed for the fit to the real components. The resulting slope is given by equation (7) and the corresponding intercept is defined by equation (8).

$$\Delta_n=\frac{\sum_{i=0}^{I}C_i\sum_{i=0}^{I}iC_iB_{in}-\sum_{i=0}^{I}iC_i\sum_{i=0}^{I}C_iB_{in}}{\Sigma C_i\Sigma i^2C_i-(\Sigma iC_i)^2} \qquad (7)$$

$$\delta_n=\frac{\sum_{i=0}^{I}i^2C_i\sum_{i=0}^{I}iC_iB_{in}-\sum_{i=0}^{I}iC_i\sum_{i=0}^{I}iC_iB_{in}}{\sum_{i=0}^{I}C_i\sum_{i=0}^{I}i^2C_i-\left(\sum_{i=0}^{I}iC_i\right)^2} \qquad (8)$$

In the absence of any blade resonance (and the presence of numerically perfect processing), all of the resulting slopes would be zero-valued. Zero-valued slopes reflect identical spectral content in each of the plurality of order-normalized spectra. It also indicates identical ensemble average content at each shaft speed segregated.

In the event of blade resonance, the slopes of all participating harmonic terms become non-zero, indicating the change in spectral phase with shaft speed introduced by the resonance. Hence these sixty-two slope coefficients reflect the Resonant Signal 106, which may be computed from these values. In contrast, the sixty-two intercepts are (fundamentally) unaffected by the presence or absence of a resonance. These Fourier coefficients represent the synchronous content of the microphone signal averaged over all perturbations in speed. Thus, the Fourier coefficient slopes reflect the characteristic Doppler signal 64 while the Fourier intercept coefficients define the content of the periodic background noise 66. More specifically, the intercepts are the Fourier coefficients of the synchronous ensemble average of all revolutions captured in the plurality of ensembles, collectively. The slopes are the Fourier coefficients of the first-difference approximation of the derivative of this synchronous ensemble with respect to machine speed. Hence, the desired Resonant Signal 106 may be obtained by transforming these coefficients back to the shaft-angle (time) domain as follows. A Fourier-based synthesizer, shown at block 140, reconstructs the Resonant Signal 106 from the sixty-two Fourier slope coefficients. This is done by direct synthesis, a process wherein the thirty-one real slope coefficients multiply thirty-one sampled unit amplitude cosine waves of corresponding harmonic order and the thirty-one imaginary slope coefficients multiply thirty-one sampled unit amplitude sine waves of corresponding harmonic order and all sixty-two products are summed at each sample point. Synthesizer 140 also forms the Hilbert transform of the Resonant Signal 106 simultaneously via exactly the same process. The same Fourier slope coefficients are involved but they are arranged differently, producing the required 90° phase shift in the frequency domain.

In the process of synthesis, it is not necessary to utilize the same number of samples per revolution used in the initial acquisition of data. Using fewer than the sixty-four points per revolution with which the ensemble averages were gathered would result in the loss of information. Using more does not add knowledge as the bandwidth of the data is now fixed. Additional samples merely interpolate the computed answers and provide sample points at convenient intervals. It is also possible to impose an arbitrary phase shift upon the synthesized function to change its temporal alignment. Equation (9) defines the synthesis of the Resonant Signal 106; equation (10) defines the synthesis of its Hilbert transform.

$$R(b)=\sum_{n=1}^{N}\left\{\Omega_n\cos\left[n\left(2\pi\frac{(b-1)}{B}-d\right)\right]+ \right. \qquad (9)$$
$$\left. \Delta_n\sin\left[n\left(2\pi\frac{(b-1)}{B}-d\right)\right]\right\}$$

$$H\{R(b)\}=\sum_{n=1}^{N}\left\{\Omega_n\sin\left[n\left(2\pi\frac{(b-1)}{B}-d\right)\right]- \right. \qquad (10)$$
$$\left. \Delta_n\cos\left[n\left(2\pi\frac{(b-1)}{B}-d\right)\right]\right\}$$

where

R(b)=the acoustic Resonant Signal 108;

H{R(b)}=the Hilbert transform of the acoustic Resonant Signal 108;

B=the number of blades 14 in a row of blades;

b=the blade number ($1 \leq b \leq B$);

d=an azimuth angle between the sensors (radian), a negative angle shifts the trace to the left for earlier arrival or positive to shift the trace to the right representing a delay;

A larger number of points per revolution (typically one per blade) is desirable for purpose of display and interrogation. Point-per-blade resolution implies 200–300 points per revolution for most turbines. Since the data is (typically) band limited by an anti-aliasing selected to exclude the group passage frequency (a sub-multiple of the number of blades) it is neither necessary nor desirable to sample at this high rate. Achieving point-per-blade output sampling through the synthesis process permits the acquisition hardware to be designed without regard to the specifics of the rotor being monitored. A smaller and more convenient number (typically a binary number) of samples may be gathered and processed each revolution. Use of an arbitrary phase shift permits aligning data from two microphones located at different azimuths within the turbine casing or collected with reference to different tachometers. The Resonant Amplitude and the Resonant Frequency may then be computed via magnitude resolver and frequency resolver in the same manner as described in FIG. 11.

FIG. 13 depicts a first alternate embodiment of the present invention. In this embodiment, the method of data acquisition, averaging and processing is changed. As in the first embodiment, the band-limited microphone signal is synchronously sampled by the analog-to-digital converter 74 using a sample rate of sixty-four times the nominal shaft speed. Again, the sample rate may be varied, and it is within the scope of the invention to practice the processes described herein using different sample rates. Also, as in the first embodiment, the sample control circuit 82 functions to synchronize the first sample to the arrival of the tachometer target 18 at the tachometer probe 20. The output of the analog-to-digital converter is passed through buffer 84.

At the conclusion of each revolution, a sixty-four point time history is passed from the buffer 84 to a Fourier decomposition processor, indicated at block 120. As in the first preferred embodiment, the Fourier decomposition 120 cannot perform a simple unweighted FFT because some revolutions are (very slightly) under-sampled while others are (very slightly) over-sampled from a nominal sixty-four samples per revolution. Instead, a co-location curve fitter and knowledge of the exact shaft rotational speed associated with the revolution are employed. An harmonic series of thirty-one (very slightly) over and/or under sampled sine and cosine waves plus a mean (DC) value are curve fit to each ensemble. The output of this process is a complex order-normalized spectrum, indicated at line 142, reflecting the spectral content of the most recently completed shaft revolution.

Each order-normalized spectrum has a real (cosine) component and an imaginary (sine) component. The real (cosine) and imaginary (sine) components of the order-normalized spectrum are subjected to the action of an ensemble averager, indicated at block 148 which forms and accumulates the averaged real and imaginary order-normalized spectrum in accordance with equations (11) and (12).

$$A_n = \frac{1}{J} \sum_{j=1}^{J} A_{jn} \tag{11}$$

$$B_n = \frac{1}{J} \sum_{j=1}^{J} B_{jn} \tag{12}$$

where $A_n$=averaged real component value of the nth harmonic of shaft speed;

$A_{jn}$=real component value for the nth harmonic during the jth revolution;

$B_n$=averaged imaginary component value of the nth harmonic of shaft speed;

$B_{jn}$=imaginary component value for the nth harmonic during the jth revolution;

j=a revolution index ($1 \leq j \leq J$); and

J=number of revolutions averaged.

As each revolution is captured, the period detector 92 measures the time interval between successive tachometer probe 20 output pulses to a precision of 50 Ns, as previously discussed. This period measurement is used as an address by speed deviation look-up table, indicated at block 154. The output of the deviation look-up table is the instantaneous speed deviation. The instantaneous speed deviation is simply a number proportional to the deviation of the turbine from its nominal speed during the most recent revolution. When each order-normalized spectrum 142 is produced, it is multiplied by the (scaler) instantaneous speed deviation by a multiplier, shown at block 158, resulting in the speed-weighted spectrum, shown at line 160. The real (cosine) and imaginary (sine) components of this order-normalized spectrum 160 are subjected to the action of an ensemble averager, shown at block 166, which forms and accumulates the averaged real and imaginary order-normalized spectrum in accordance with equations (13) and (14).

$$\alpha_n = \frac{1}{J} \sum_{j=1}^{J} S_j A_{jn} \tag{13}$$

$$\beta_n = \frac{1}{J} \sum_{j=1}^{J} S_j B_{jn} \tag{14}$$

where $\alpha_n$=averaged speed-weighted real component value of the nth harmonic of shaft speed;

$\beta_n$=averaged speed-weighted imaginary component of the nth harmonic of shaft speed;

$S_j$=speed deviation during the jth revolution;

The deviation look-up table 154 also passes the instantaneous speed deviation to a deviation statistics module, shown at block 172, every revolution. The deviation statistics module 172 averages the mean value of the speed deviations in accordance with equation (15) and the mean-square value of the deviations in accordance with equation (16).

$$\mu = \frac{1}{J} \sum_{j=1}^{J} S_j \tag{15}$$

$$\sigma^2 = \frac{1}{J} \sum_{j=1}^{J} S_j^2 \tag{16}$$

The actions just described are repeated over a pre-defined observation interval, typically 30 minutes. Once again, the acquisition of data takes place in real-time, where every revolution that occurs within the observation interval contributes to the averages formed. At the end of this observation interval the averaged spectra and the speed deviation statistics accumulated over the acquisition interval are passed to a curve fitter, shown at block 178.

The curve-fitter 178 fits a linear function of shaft speed deviation to each of the real components of the averaged spectra in accordance with equation (17). It simultaneously fits a linear function of shaft speed deviation to each of the imaginary components of the spectra in accordance with equation (18).

$$A_n(S) = \Omega_n + \omega_n \quad (17)$$

$$B_n(S) = \Delta_n + \delta_n \quad (18)$$

where

S=the instantaneous speed deviation of the turbine;

$A_n(S)$=the cosine coefficient for the nth order term at speed deviation S;

$\Omega_n$=is the slope of the linear $A_n$ function;

$\omega_n$=the intercept of the linear $A_n$ function;

$B_n(S)$=the sine coefficient for the nth order term at speed deviation S;

$\Delta_n$=the slope of the linear $B_n$ function; and $\delta_n$=the intercept of the linear $B_n$ function.

The N required $\Omega_n$ and $\Delta_n$ slopes and the N required $\omega_n$ and $\delta_n$ intercepts are derived by "least squares" minimization in a manner synonymous with that derived for the curve fitter 128 of FIG. 12. The resulting equations implemented by the curve-fitter 178 are specified by equations (19) and (20), following.

$$\begin{bmatrix} \Omega_n \\ \omega_n \end{bmatrix} = \frac{1}{\sigma^2 - \mu^2} \begin{bmatrix} 1 & -\mu \\ -\mu & \sigma^2 \end{bmatrix} \begin{bmatrix} \alpha_n \\ A_n \end{bmatrix} \quad (19)$$

$$\begin{bmatrix} \Delta_n \\ \delta_n \end{bmatrix} = \frac{1}{\sigma^2 - \mu^2} \begin{bmatrix} 1 & -\mu \\ -\mu & \sigma^2 \end{bmatrix} \begin{bmatrix} \beta_n \\ B_n \end{bmatrix} \quad (20)$$

One significant advantage of this method over the first embodiment of FIG. 12 is that it does not require the speed segregated ensemble averages. This means that neither the speed range nor the resolution to which it is segregated need to be pre-defined. Further, only two averaged spectra, are required. These consume the same amount of memory as two (of the plurality) of the speed segregated averages in the first embodiment and the technology it supersedes. In detriment, one Fourier decomposition must be performed for every revolution, where the first embodiment required only two such decompositions per averaging interval.

It is noted that a simple unweighted fast Fourier transform (FFT) could be substituted for the co-location fitting process in the Fourier decomposition 120 if the sample control 82 employed a phase-locked loop, shaft encoder or other means of making the sample rate applied to analog-to-digital converter 74 exactly a fixed number (sixty-four for example) per revolution. This concept is expanded upon in the second alternate embodiment discussed hereinafter.

FIG. 14 presents the second alternate embodiment wherein a sample control circuit, shown at block 180, uses a multiple pulse per revolution encoder affixed to the shaft 16 or alternate means based upon existing phase-locked loop (PLL) or period locked loop with phase assertion (PLL/PA) technology to derive a sample rate proportional to the instantaneous rotational speed of the shaft 16 and apply it to the analog-to-digital converter 74. This results in an angle history being stored in the buffer 84 which has amplitude samples acquired as a sequence of evenly spaced shaft rotational angles, regardless of the instantaneous speed of the turbine. A simple unweighted FFT of the angle history produces an order normalized spectrum, synonymous in form and content with the output of the Fourier decomposition means 120 discussed in FIG. 13.

In this embodiment, an FFT is not be taken at this step. Instead, the angle history stored in the buffer 84 is acted upon by an ensemble averager, shown at block 186, which performs its synchronous average in the angle (time) domain, producing an averaged angle history. As in the embodiment of FIG. 13, the period detector 92 and the shaft speed deviation look-up 154 function in consort to provide the instantaneous speed deviation to a multiplier, shown at block 190, which multiplies the scaler instantaneous speed deviation by the instantaneous angle history forming a speed-weighted angle history. A second ensemble averager, shown at block 194, averages this speed-weighted angle history function in the manner previously described and produces the speed-weighted average angle history.

As described in the previous methods, the actions just described are repeated over a pre-defined observation interval, typically 30 minutes. The acquisition of data takes place in real-time with every revolution that occurs within the observation interval contributing to the averages formed. At the end of this observation interval the averaged angle histories are subjected to an unweighted FFT process by the Fourier decomposition modules shown at blocks 198a and 198b. This results in the averaged complex order-normalized spectrum and the averaged complex speed-weighted order-normalized spectrum since the processes of Fourier transformation and synchronous ensemble averaging are distributive. The results of the synchronous ensemble averaging of this embodiment are synonymous with the corresponding results of FIG. 13. The spectra, the mean shaft speed deviation and the mean-square shaft speed deviation are passed to the curve fitter, shown at block 178, that processes them in the identical manner as in the first alternate embodiment of FIG. 13, to generate the linear shaft speed functions which may be Fourier synthesized to determine the Resonant Signal 108 and the Resonant signal Hilbert transform 110.

The fundamental advantages of this second alternate embodiment over the first alternate embodiment are that a simple unweighted FFT may be used as the mechanism of Fourier decomposition 198 and that such decomposition must only be applied to two angle (time) histories per averaging interval.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for detecting a resonantly vibrating blade in a row of blades secured to a shaft rotating about a rotor axis, in an operating turbine, comprising:

an acoustic sensor positioned on a stationary member with respect to said shaft to receive sound waves emanating from said rotating blades as said blades rotate about said rotor axis and to provide an output signal representative said received sound waves, said acoustic sensor positioned with respect to said shaft so that said vibrating blade approaches and departs from said acoustic sensor in the course of one rotation of said shaft about said rotor axis;

reference means for obtaining a reference signal indicative of shaft position at least once each time said shaft completes a revolution about said rotor axis and for determining shaft speed;

sampling means for sampling said sensor output signal to obtain samples related to shaft position as said shaft completes a multiplicity of revolutions at a plurality of different shaft speeds;

first memory means for temporarily storing the shaft speed from the reference means and a corresponding plurality of samples synchronized with the shaft position obtained by said sampling means, said plurality of samples together comprising a sample series representing at least one shaft rotation;

ensemble averager means for averaging multiple sample series to develop a plurality of synchronous ensemble averages differentiated by shaft speed;

second memory means for storing the plurality of synchronous ensemble averages differentiated by shaft speed, and an accompanying shaft speed histogram;

Fourier decomposition means for generating a plurality of complex order-normalized spectra differentiated by shaft speed from the synchronous ensemble averages stored in the second memory means, each complex order-normalized spectrum having a real component and an imaginary component;

curve fitter means for curve fitting the plurality of complex order-normalized spectra using the shaft speed histogram as a weighting function to generate a series of generally linear shaft speed functions fit to the real and imaginary Fourier coefficients of the complex order-normalized spectra, wherein for a linear curve fit, the Fourier slope coefficients represent a characteristic Doppler signal and the Fourier intercept coefficients represent periodic background noise; and synthesis means for constructing a resonant signal characterizing the vibration of the resonantly vibrating blade from the generally linear shaft speed functions generated by the curve fitter means, an instantaneous amplitude thereof being used to identify the resonantly vibrating blade in the monitored row of blades.

2. The apparatus of claim 1 wherein the first memory means temporarily stores sixty-four time spaced samples reflecting acoustic pressure variations during a single most recent revolution of the shaft.

3. The apparatus of claim 1 wherein the sensor output signal is processed in real-time and every shaft revolution is characterized by a period.

4. The apparatus of claim 1 wherein the curve fitter means fits a linear function to each of the real components of the complex order-normalized spectrum in accordance with the equation:

$$A_{in} = \Omega_n i + \omega_n$$

where $A_{in}$=a cosine coefficient for the nth order term of the ith speed average;

$\Omega_n$=a slope of a best fit straight line through the $A_{in}$ data points;

$\omega_n$=an intercept of the straight line;

i=an index to the speed segregation, wherein ($0 \leq i \leq I$), I=a number of shaft speed categories segregated during data acquisition; and n=a harmonic order number ($1 \leq n \leq N$), N=the maximum harmonic order decomposed.

5. The apparatus of claim 4 wherein the curve fitter means substantially simultaneously fits a linear function to each of the imaginary components of the complex order-normalized spectrum in accordance with the equation:

$$B_{in} = \Delta_n i + \delta_n$$

where $B_{in}$=a sine coefficient for the nth order term of the ith speed average;

$\Delta_n$=a slope of a "best fit" straight line through the $B_{in}$ data points;

$\delta_n$=an intercept of the straight line;

i=an index to the speed segregation, wherein ($0 \leq i \leq I$), I=a number of shaft speed categories segregated during data acquisition; and n=a harmonic order number, wherein ($1 \leq n \leq N$), N=the maximum harmonic order decomposed.

6. The apparatus of claim 1 wherein the synthesis means constructs the resonant signal from the Fourier slope coefficients and forms a Hilbert transform of the resonant signal via direct synthesis.

7. The apparatus of claim 6 wherein the synthesis means constructs the resonant signal from the Fourier slope coefficients via direct synthesis by multiplying the real slope coefficients by sampled unit amplitude cosine waves of a corresponding harmonic order and multiplying the imaginary slope coefficients by sampled unit amplitude sine waves of a corresponding harmonic order and summing all of the resulting products at each sample point.

8. The apparatus of claim 7 wherein the Hilbert transform of the resonant signal is formed by direct synthesis substantially simultaneously using the same Fourier slope coefficients, wherein the Fourier slope coefficients are arranged to produce a 90° phase shift in the frequency domain.

9. The apparatus of claim 7 wherein an arbitrary phase shift is imposed upon the synthesized signal to change a temporal alignment of the synthesized signal to align data from more than one acoustic pressure sensor means located at different azimuths relative to the shaft, the synthesis of the resonant signal defined in accordance with the equation:

$$R(b) = \sum_{n=1}^{N} \left\{ \Omega_n \cos\left[ n\left( 2\pi \frac{(b-1)}{B} - d \right) \right] + \Delta_n \sin\left[ n\left( 2\pi \frac{(b-1)}{B} - d \right) \right] \right\}$$

and the synthesis of the Hilbert transform of the resonant signal defined in accordance with the equation:

$$H\{R(b)\} = \sum_{n=1}^{N} \left\{ \Omega_n \sin\left[ n\left( 2\pi \frac{(b-1)}{B} - d \right) \right] - \Delta_n \cos\left[ n\left( 2\pi \frac{(b-1)}{B} - d \right) \right] \right\}$$

where

R(b)=the resonant signal;

H{R(b)}=the Hilbert transform of the resonant signal;

B=the number of blades in a row of blades;

b=a blade number ($1 \leq b \leq B$);

d=an azimuth angle between the sensors;

n=a harmonic order number ($1 \leq n \leq N$);

N=a maximum harmonic order decomposed;

$\Delta_n$=slope of a best fit straight line through the $B_{in}$ data points, $B_{in}$=a sine coefficient for the nth order term of the of the ith speed average; and $\Omega_n$=slope of a best fit straight line through the $A_{in}$ data points, $A_{in}$=a cosine coefficient for the nth order term of the ith speed average.

10. The apparatus of claim 9 wherein the azimuth angle between the sensors (d) is negative to shift a trace from a sensor located to receive a later blade arrival.

11. The apparatus of claim 9 wherein the azimuth angle between the sensors (d) is positive to shift a trace from a sensor located to receive an earlier blade arrival.

12. An apparatus for detecting a resonantly vibrating blade in a row of blades secured to a shaft rotating about a rotor axis from data acquired at more than two different operating shaft rotational speeds, in an operating turbine, comprising:

an acoustic sensor positioned on a stationary member with respect to said shaft to receive sound waves emanating from said rotating blades as said blades rotate about said rotor axis and to provide an output representative of said received sound waves, said acoustic sensor positioned with respect to said shaft so that said vibrating blade approaches and departs from said acoustic sensor in the course of one rotation of said shaft about said rotor axis;

reference means for obtaining a reference signal indicative of shaft position at least once each time said shaft completes a revolution about said rotor axis and for determining shaft speed;

a sample control circuit for establishing a rate for sampling the sensor output signal over a multiplicity of shaft revolutions;

first memory means for temporarily storing a plurality of samples of said sensor output signal the data acquisition means, said plurality of samples together comprising a time history per blade revolution;

Fourier decomposition means for generating a multiplicity of complex order-normalized spectra from the time history, each complex spectrum having a real component and an imaginary component, the spectrum reflecting the spectral content of a single most recently completed shaft revolution;

first ensemble averager means for forming and accumulating an average complex order-normalized spectrum from the multiplicity of complex order-normalized spectra;

an address deviation look-up table cooperating with the reference means for generating an instantaneous speed deviation;

multiplier means for multiplying the complex order-normalized spectrum associated with the most recent revolution and the associated instantaneous speed deviation to generate a multiplicity of speed weighted complex order-normalized spectra;

second ensemble averager means for forming and accumulating an average speed weighted complex order-normalized spectrum from the multiplicity of speed weighted complex order-normalized spectra;

a deviation statistics means for averaging instantaneous shaft speed deviations to generate deviation statistics;

curve fitter means for simultaneously fitting a linear function of the shaft speed deviation to the real and the imaginary components of the averaged complex order-normalized spectrum and the averaged speed weighted complex order-normalized spectrum using the deviation statistics, to generate a series of generally linear shaft speed functions and;

synthesis means for constructing a resonant signal characterizing the vibration of the resonantly vibrating blade from the generally linear shaft speed functions generated by the curve fitter means, an instantaneous amplitude thereof being used to identify the resonantly vibrating blade in the monitored row of blades.

13. The apparatus of claim 12 wherein the deviation statistics comprise a mean value and a mean square value of the shaft speed deviations.

14. The apparatus of claim 12 wherein the reference means comprises a tachometer and a period detector, the period detector for measuring time intervals between successive tachometer pulses, wherein the first sample point is synchronized with the tachometer.

15. The apparatus of claim 12 wherein the Fourier decomposition means comprises a co-location curve fitter utilizing the shaft rotational speed per shaft revolution to fit a harmonic series of sine and cosine waves plus a mean value to the time history data to generate the complex order-normalized spectrum.

16. The apparatus of claim 12 wherein the first ensemble averager means forms and accumulates the average real and the average imaginary components of the complex order-normalized spectra in accordance with the equations:

$$A_n = \frac{1}{J} \sum_{j=1}^{J} A_{jn}; \text{ and}$$

$$B_n = \frac{1}{J} \sum_{j=1}^{J} B_{jn}, \text{ wherein}$$

$A_n$=average real component value of the nth harmonic of shaft speed;

$B_n$=average imaginary component value of the nth harmonic of shaft speed;

$A_{jn}$=real component value of the nth harmonic during the jth revolution;

$B_{jn}$=imaginary component value of the nth harmonic during the jth revolution;

n=a harmonic order number ($1 \leq n \leq N$), N=a maximum harmonic order decomposed;

j=a revolution index ($1 \leq j \leq J$); and

J=number of revolutions averaged.

17. The apparatus of claim 12 wherein the second ensemble averager means forms and accumulates the average speed weighted real and the average speed weighted imaginary components of the speed weighted complex order-normalized spectra in accordance with the equations:

$$\alpha_n = \frac{1}{J} \sum_{j=1}^{J} S_j A_{jn}; \text{ and}$$

$$\beta_n = \frac{1}{J} \sum_{j=1}^{J} S_j B_{jn}, \text{ wherein}$$

$\alpha_n$=average speed weighted real component of the nth harmonic of shaft speed;

$\beta_n$=average speed weighted imaginary component of the nth harmonic of shaft speed;

$S_j$=speed deviation during the jth revolution;

$A_{jn}$=real component value of the nth harmonic during the jth revolution;

$B_{jn}$=imaginary component value of the nth harmonic during the jth revolution;

n=a harmonic order number ($1 \leq n \leq N$), N=a maximum harmonic order decomposed;

j=a revolution index (1≦j≦J); and

J=number of revolutions averaged.

18. The apparatus of claim 12 wherein the sensor output signal is processed in real time such that every revolution of the shaft contributes to the averages formed by the first and second ensemble averager means.

19. The apparatus of claim 12 wherein the sample rate is a fixed number per revolution.

20. The apparatus of claim 19 wherein the fixed number per revolution is sixty-four.

21. The apparatus of claim 19 wherein the Fourier decomposition means performs a simple unweighted fast Fourier transform.

22. The apparatus of claim 19 wherein the sample control circuit comprises a shaft encoder to fix the sample number per shaft revolution.

23. The apparatus of claim 19 wherein the sample control circuit comprises a phase locked loop having a phase assertion means for fixing the sample number per shaft revolution.

24. An apparatus for detecting a resonantly vibrating blade in a row of blades secured to a shaft rotating about a rotor axis in an operating turbine, from data acquired at more than two different operating shaft rotational speeds, to identify the vibrating blade, comprising:

an acoustic sensor positioned on a stationary member with respect to said shaft to receive sound waves emanating from said rotating blades as said blades rotate about said rotor axis and to provide an output signal representative of said received sound waves, said acoustic sensor positioned with respect to said shaft so that said vibrating blade approaches and departs from said acoustic sensor in the course of one rotation of said shaft about said rotor axis;

reference means for obtaining a reference signal indicative of shaft position at least once each time said shaft completes a revolution about said rotor axis and for determining shaft speed;

a sample control circuit for establishing a rate for sampling the output signal sensor over a multiplicity of shaft revolutions;

first memory means for temporarily storing a plurality of samples of the sensor output signal, said plurality of samples together comprising an instantaneous angle history;

a period detector circuit cooperating with a shaft speed deviation look-up table for generating an instantaneous speed deviation;

a deviation statistics module for averaging instantaneous speed deviations to generate deviation statistics;

first ensemble averager means for generating an average angle history from the instantaneous angle history;

multiplier means for multiplying the instantaneous speed deviation and the instantaneous angle history to generate a speed weighted angle history;

second ensemble averager means for generating an average speed weighted angle history from the speed weighted angle history;

first Fourier decomposition means for generating an average complex order-normalized spectrum from the average angle history;

second Fourier decomposition means for generating an average speed weighted complex order-normalized spectrum from the average speed weighted angle history;

curve fitter means for simultaneously fitting a linear function of the shaft speed deviation to the real and the imaginary components of the averaged complex order-normalized spectrum and the averaged speed weighted complex order-normalized spectrum using the deviation statistics, to generate a series of generally linear shaft speed functions;

synthesis means for constructing a resonant signal characterizing the vibration of the resonantly vibrating blade from the generally linear shaft speed functions generated by the curve fitter means, an instantaneous amplitude thereof being used to identify the resonantly vibrating blade in the monitored row of blades.

25. The apparatus of claim 24 wherein the sample control circuit generates a sample rate which is a fixed number per shaft revolution.

26. The apparatus of claim 25 wherein the sample rate is proportional to the instantaneous rotational speed of the shaft.

27. The apparatus of 26 wherein the sample control circuit comprises a multiple pulse per revolution encoder affixed to the shaft.

28. The apparatus of 26 wherein the sample control circuit comprises a phase locked loop having a phase assertion means for fixing the sample number per shaft revolution.

29. The apparatus of claim 24 wherein the first and the second Fourier decomposition means each perform a simple unweighted fast Fourier transform.

30. The apparatus of claim 24 wherein the acoustic sensor and the reference means operate in real time such that every revolution of the shaft contributes to the average angle history.

31. The apparatus of claim 25 wherein the fixed number is sixty-four.

32. The apparatus of claim 24 wherein the acoustic sensor includes an analog-to-digital convertor for converting the sensor output signal to digital signals to generate a shaft angle history comprising amplitude samples acquired as a sequence of evenly spaced shaft rotational angles.

33. The apparatus of claim 24 wherein the deviation statistics comprise a mean value and a mean square value of the shaft speed deviations.

34. The apparatus of claim 24 wherein the curve fitter means fits a linear function of the shaft speed deviation to the real and the imaginary components of the average complex order-normalized spectrum and the average speed weighted complex order-normalized spectrum in accordance with the equations:

$$A_n(S)=\Omega_n S+\omega_n;$$

and $$B_n(S)=\Delta_n S+\delta_n,$$

wherein

S=the instantaneous speed deviation of the shaft;

n=a harmonic order number (1≦n≦N), N=the maximum harmonic order decomposed;

$A_n(S)$=a cosine coefficient for the nth order term at speed deviation S;

$\Omega_n$=a slope of the linear $A_n$ function;

$\omega_n$=an intercept of the linear $A_n$ function;

$B_n(S)$=a sine coefficient for the nth order term at speed deviation S;

$\Delta_n$=a slope of the linear $B_n$ function; and $\delta_n$=an intercept of the linear $B_n$ function.

35. The apparatus of claim 34 wherein the required $\Omega_n$ and $\omega_n$ slopes and the required $\Delta_n$ and $\delta_n$ intercepts are derived by least squares minimization.

36. A method of isolating from periodic background noise an acoustic signal characterizing the vibration of a resonantly vibrating blade in a row of turbine blades secured to a shaft rotating about a rotor axis from data acquired at more than two different operating shaft rotational speeds to identify the vibrating blade, comprising the steps of:

acquiring acoustic pressure wave data from pressure waves emanating from the rotating blades from one or more stationary sensors located proximate the turbine blades;

identifying the angular position of the shaft and the shaft speed at least once each time said shaft completes a revolution about said rotor axis;

sampling the pressure wave data acquired by the one or more sensor at a predetermined sample rate;

temporarily storing in a first memory the shaft speed and a corresponding plurality of samples of the pressure wave data synchronized with the shaft position, said plurality of samples together comprising a sample series representing at least one shaft rotation;

averaging multiple sample series to develop a plurality of synchronous ensemble averages differentiated by shaft speed;

storing in a second memory the plurality of synchronous ensemble averages differentiated by shaft speed and an accompanying shaft speed histogram;

performing a Fourier decomposition on the stored synchronous ensemble averages to generate a plurality of complex order-normalized spectra differentiated by shaft speed, each complex order-normalized spectrum having a real component and an imaginary component;

curve fitting the plurality of complex order-normalized spectra using the shaft speed histogram as a weighting function to generate a series of generally linear shaft speed functions fit to the real and imaginary Fourier coefficients of the complex order-normalized spectra, wherein the Fourier slope coefficients represent a characteristic Doppler signal and the Fourier intercept coefficients represent periodic background noise;

constructing a resonant signal characterizing the vibration of the resonantly vibrating turbine blade from the generally linear shaft speed functions; and determining an instantaneous amplitude of the constructed resonant signal to identify the vibrating blade in the monitored row of blades.

37. A method of isolating from periodic background noise an resonant signal characterizing the vibration of a resonantly vibrating turbine blade in a row of turbine blades secured to a shaft rotating about a rotor axis from data acquired at more than two different operating shaft rotational speeds to identify the vibrating blade, comprising the steps of:

acquiring acoustic pressure wave data from pressure waves emanating from the rotating blades from one or more stationary sensors located proximate the turbine blades;

identifying the angular position of the shaft and the shaft speed at least once each time said shaft completes a revolution about said rotor axis;

sampling the pressure wave data at a predetermined sample rate;

temporarily storing in a first memory a plurality of samples of the data acquired, said plurality of samples together comprising a time history per blade revolution;

performing a Fourier decomposition on the time history data to generate a multiplicity of complex order-normalized spectra, each complex spectrum having a real component and an imaginary component, the spectrum reflecting the spectral content of a single most recently completed shaft revolution;

forming and accumulating an average complex order-normalized spectrum from the multiplicity of complex order-normalized spectra;

generating an instantaneous speed deviation from the angular position and the speed of the shaft using an address deviation look-up table;

multiplying the complex order-normalized spectrum associated with the most recent revolution and the associated instantaneous speed deviation to generate a multiplicity of speed weighted complex order-normalized spectra;

averaging the multiplicity of speed weighted complex order-normalized spectra to form and accumulate an average speed weighted complex order-normalized spectrum;

generating deviation statistics based on instantaneous shaft speed deviations;

curve fitting a linear function of the shaft speed deviation to the real and the imaginary components of the averaged complex order-normalized spectrum and the averaged speed weighted complex order-normalized spectrum using the deviation statistics, to generate a series of generally linear shaft speed functions;

constructing a resonant signal characterizing the vibration of the resonantly vibrating turbine blade from the generally linear shaft speed functions via Fourier-based synthesis; and determining an instantaneous amplitude of the constructed resonant signal to identify the resonantly vibrating blade in the monitored row of blades.

38. A method of isolating from periodic background noise an resonant signal characterizing the vibration of a resonantly vibrating blade in a row of turbine blades secured to a shaft rotating about a rotor axis from data acquired at more than two different operating shaft rotational speeds to identify the vibrating blade, comprising the steps of:

acquiring acoustic pressure wave data from pressure waves emanating from the rotating blades from one or more sensors located proximate the turbine blades;

identifying the angular position of the shaft and the speed of the shaft at least once each time said shaft completes a revolution about said rotor axis;

sampling the pressure wave data acquired at a predetermined sample rate;

temporarily storing in a first memory a plurality of samples of the sampled data, said plurality of samples together comprising an instantaneous angle history;

generating an instantaneous speed deviation using a period detector circuit cooperating with a shaft speed deviation look-up table;

generating deviation statistics based on instantaneous shaft speed deviations;

generating an average angle history from the instantaneous angle history;

multiplying the instantaneous speed deviation and the instantaneous angle history to generate a speed weighted angle history;

generating an average speed weighted angle history from the speed weighted angle history;

generating an average complex order-normalized spectrum by performing a Fourier decomposition on the average angle history;

generating an average speed weighted complex order-normalized spectrum by performing a Fourier decomposition on the average speed weighted angle history;

fitting a linear function of the shaft speed deviation to the real and the imaginary components of the averaged complex order-normalized spectrum and the averaged speed weighted complex order-normalized spectrum substantially simultaneously using the deviation statistics to generate a series of generally linear shaft speed functions;

constructing a resonant signal characterizing the vibration of the resonantly vibrating turbine blade by performing Fourier-based synthesis on the linear shaft speed functions; and determining an amplitude of the constructed resonant signal to identify the resonantly vibrating blade in the monitored row of blades.

* * * * *